(12) United States Patent
Ragot et al.

(10) Patent No.: US 11,207,268 B2
(45) Date of Patent: Dec. 28, 2021

(54) EDIBLE PRODUCT COMPRISING RECONSTITUTED PLANT MATERIAL

(71) Applicants: Schweitzer-Mauduit International, Inc., Alpharetta, GA (US); SWM Luxembourg s.a.r.l., Luxembourg (LU)

(72) Inventors: Philippe Ragot, Le Mans (FR); Esther Pons, Pessac (FR); Bernard Mompon, Vannes (FR); Cedric Rousseau, Le Mans (FR)

(73) Assignee: Schweitzer-Mauduit International, Inc., Alpharetta, GA (US)

( * ) Notice: Subject to any disclaimer, the term of this patent is extended or adjusted under 35 U.S.C. 154(b) by 50 days.

(21) Appl. No.: 16/552,073

(22) Filed: Aug. 27, 2019

(65) Prior Publication Data

US 2020/0101013 A1 Apr. 2, 2020

Related U.S. Application Data

(63) Continuation of application No. 14/448,560, filed on Jul. 31, 2014, now Pat. No. 10,751,282.

(60) Provisional application No. 61/861,541, filed on Aug. 2, 2013.

(51) Int. Cl.
| | | |
|---|---|---|
| A61K 9/00 | (2006.01) | |
| A23F 3/22 | (2006.01) | |
| A23F 3/34 | (2006.01) | |
| A23F 5/28 | (2006.01) | |
| A23F 3/38 | (2006.01) | |
| A23F 5/36 | (2006.01) | |
| A23F 3/30 | (2006.01) | |
| A23G 1/30 | (2006.01) | |
| A23G 1/00 | (2006.01) | |
| A23L 33/21 | (2016.01) | |
| A23L 27/10 | (2016.01) | |
| A23L 33/105 | (2016.01) | |
| A23P 20/00 | (2016.01) | |
| A61K 36/185 | (2006.01) | |
| A61K 36/48 | (2006.01) | |
| A61K 36/53 | (2006.01) | |
| A61K 36/534 | (2006.01) | |
| A61K 36/54 | (2006.01) | |
| A61K 36/74 | (2006.01) | |
| A61K 36/82 | (2006.01) | |
| A61K 36/00 | (2006.01) | |

(52) U.S. Cl.
CPC ............ *A61K 9/0056* (2013.01); *A23F 3/22* (2013.01); *A23F 3/30* (2013.01); *A23F 3/34* (2013.01); *A23F 3/385* (2013.01); *A23F 5/28* (2013.01); *A23F 5/36* (2013.01); *A23G 1/002* (2013.01); *A23G 1/30* (2013.01); *A23L 27/10* (2016.08); *A23L 33/105* (2016.08); *A23L 33/21* (2016.08); *A23P 20/00* (2016.08); *A61K 36/185* (2013.01); *A61K 36/48* (2013.01); *A61K 36/53* (2013.01); *A61K 36/534* (2013.01); *A61K 36/54* (2013.01); *A61K 36/74* (2013.01); *A61K 36/82* (2013.01); *A61K 36/00* (2013.01)

(58) Field of Classification Search
CPC ...... A23F 3/22; A23F 3/30; A23F 3/34; A23F 3/385; A23F 5/28; A23F 5/36; A23G 1/002; A23G 1/30; A23L 27/10; A23L 33/105; A23L 33/21; A23P 20/00; A61K 36/00; A61K 36/185; A61K 36/48; A61K 36/53; A61K 36/534; A61K 36/54; A61K 36/74; A61K 36/82; A61K 9/0056; A61P 1/00; A61P 3/02
See application file for complete search history.

(56) References Cited

U.S. PATENT DOCUMENTS

| | | | |
|---|---|---|---|
| 3,353,541 A | 11/1967 | Hind et al. | |
| 3,386,449 A | 6/1968 | Hind | |
| 3,415,253 A | 12/1968 | Michaels et al. | |
| 3,420,241 A | 1/1969 | Hind et al. | |
| 3,428,053 A | 2/1969 | Schoenbaum et al. | |
| 3,429,316 A * | 2/1969 | Hess ............ | A24B 15/16 131/275 |
| 3,467,109 A | 9/1969 | Block et al. | |
| 3,483,874 A | 12/1969 | Hind | |
| 3,561,451 A | 2/1971 | Jacin et al. | |
| 3,760,815 A | 9/1973 | Deszyck | |
| 3,847,164 A | 11/1974 | Mattina et al. | |

(Continued)

FOREIGN PATENT DOCUMENTS

| | | |
|---|---|---|
| CN | 1329855 | 1/2002 |
| CN | 1565286 | 1/2005 |

(Continued)

OTHER PUBLICATIONS

Casey WJ, et al "Identification of Cellulose Fibers Isolated from Reconstituted Tobacco*" Beitrage zur Tabakforschung ( Contributions to Tobacco Research), Bd.8,H.5, Mar. 1, 1976 ; 10.2478/cttr-2013-0393. (Year: 1976).*

(Continued)

*Primary Examiner* — Aaron J Kosar
(74) *Attorney, Agent, or Firm* — Dority & Manning, P.A.

(57) ABSTRACT

The present invention relates to an edible product, which comprises a fibrous plant product and a plant extract applied thereto. Further, the invention relates to a corresponding method for producing said edible product and its use in at least one of food, food supplement, medicinal, cosmetic, well-being, nutraceutical or phytotherapeutical applications. The plants used may be all plants comprising one or more substances of interest for an edible product.

20 Claims, 16 Drawing Sheets

(56) References Cited

U.S. PATENT DOCUMENTS

| | | | |
|---|---|---|---|
| 3,860,012 A | 1/1975 | Selk | |
| 4,182,349 A | 1/1980 | Selk | |
| 4,674,519 A | 6/1987 | Keritsis et al. | |
| 4,891,232 A | 1/1990 | Dahl | |
| 5,099,862 A | 3/1992 | White et al. | |
| 5,529,796 A | 6/1996 | Gobbo | |
| 5,715,844 A | 2/1998 | Young et al. | |
| 5,724,998 A | 3/1998 | Gellatly et al. | |
| 5,765,570 A | 6/1998 | Litzinger et al. | |
| 6,761,918 B2 | 7/2004 | Pulikkottil et al. | |
| 6,818,234 B1 | 11/2004 | Nair et al. | |
| 7,001,629 B1 | 2/2006 | Mengal et al. | |
| 7,793,585 B2 | 9/2010 | Rasmussen | |
| 8,499,965 B2 | 8/2013 | Sheffield | |
| 8,597,667 B2 | 12/2013 | Mou et al. | |
| 8,734,881 B2 | 5/2014 | Yoakim et al. | |
| 9,220,296 B2 | 12/2015 | Fall et al. | |
| 2002/0132098 A1 | 9/2002 | Miyazawa et al. | |
| 2003/0004479 A1 | 1/2003 | Ueda et al. | |
| 2003/0113411 A1 | 6/2003 | Rose | |
| 2003/0187055 A1 | 10/2003 | Riker | |
| 2004/0156920 A1 | 8/2004 | Kane | |
| 2004/0180077 A1 | 9/2004 | Riker | |
| 2005/0064049 A1 | 3/2005 | Mori | |
| 2005/0088632 A1 | 4/2005 | Sadi | |
| 2005/0158252 A1 | 7/2005 | Romanowski | |
| 2005/0287278 A1 | 12/2005 | Quan et al. | |
| 2006/0165756 A1 | 7/2006 | Catani | |
| 2007/0199453 A1 | 8/2007 | Rasmussen | |
| 2007/0243273 A1 | 10/2007 | Dev et al. | |
| 2009/0047328 A1 | 2/2009 | Cunningham | |
| 2009/0169654 A1 | 7/2009 | Banerjee | |
| 2010/0032444 A1 | 2/2010 | Sheffield | |
| 2010/0196545 A1 | 8/2010 | Buffet et al. | |
| 2010/0210866 A1 | 8/2010 | Toyohara et al. | |
| 2010/0233322 A1 | 9/2010 | Fukuda | |
| 2011/0020512 A1 | 1/2011 | Masutake | |
| 2011/0236502 A1 | 9/2011 | Guillory | |
| 2013/0280320 A1 | 10/2013 | Mompon | |
| 2014/0224265 A1 | 8/2014 | Rouillard et al. | |
| 2014/0295049 A1 | 10/2014 | Ragot et al. | |
| 2015/0050371 A1 | 2/2015 | Gehling et al. | |
| 2015/0056255 A1 | 2/2015 | Ragot et al. | |
| 2015/0175810 A1 | 6/2015 | Rieland | |
| 2015/0374624 A1 | 12/2015 | Ragot et al. | |
| 2016/0255854 A1 | 9/2016 | Rousseau | |

FOREIGN PATENT DOCUMENTS

| | | | |
|---|---|---|---|
| CN | 1957777 | 5/2007 | |
| CN | 20090097787 | 4/2009 | |
| CN | 102919430 | 2/2012 | |
| CN | 103054156 | 4/2013 | |
| DE | 202010001912 | 3/2011 | |
| GB | 1180710 A | * 2/1970 | ............ A24B 15/12 |
| GB | 1341069 | 12/1973 | |
| JP | S50064500 | 5/1975 | |
| JP | H02035041 | 2/1990 | |
| JP | H8504598 | 2/1990 | |
| JP | 09163930 | 6/1997 | |
| JP | H10304822 | 11/1998 | |
| JP | 3135896 | 2/2001 | |
| JP | 2001131866 | 5/2005 | |
| JP | 2005119967 | 5/2005 | |
| JP | 2005306742 | 11/2005 | |
| JP | 2006050934 | 2/2006 | |
| JP | 2006246817 | 9/2006 | |
| JP | 2006249599 | 9/2006 | |
| JP | 2006256968 | 9/2006 | |
| JP | 2007098152 | 4/2007 | |
| JP | 2008274535 | 11/2008 | |
| JP | 2011019469 | 2/2011 | |
| JP | 2011182783 | 9/2011 | |
| KR | 20070090286 | 9/2007 | |
| KR | 20100114348 | 10/2010 | |
| SU | 1161061 | 6/1985 | |
| WO | WO9409653 | 5/1994 | |
| WO | WO0205655 | 1/2002 | |
| WO | WO03091500 | 11/2003 | |
| WO | WO2012056141 | 5/2012 | |

OTHER PUBLICATIONS

Adams et al., Analysis of the Interactions of Botanical Extract Combinations Against the Viability of Prostate Cancer Cell Lines, Mar. 2003, pp. 117-124.

Blumenthal et al., Herbal Medicine, Expanded Commission E. Monographs, 2000, pp. 393-400.

Greer, C.C. A Text-Book of Cooking; J.S. Cushing Co., Berwick & Smith Co. Norwood, MA, 1915, pp. 175-177.

Heishman et al., "Meta-analysis of the acute effects of nicotine and smoking on human performance," Psychopharmacol, 2010, vol. 210, p. 453-469.

Innovation Food Online, Sodium Alginate; https://innoviationinfood.wikispaces.com/Sodium+-Alginate published Jan. 4, 2007 online, 7 pages with extra page having google search hit with datestamp.

International Search Report and Written Opinion for PCT/EP2014/002112, dated Oct. 22, 2014, 14 pages.

Lin et al., Inhibition of Helicobacter Pylori and Associated Urease by Oregano and Cranberry Phytochemical Synergies, Applied and Environmental Microbiology, Dec. 2005, vol. 71., No. 12. pp. 8558-8564.

Lundberg et al., "Nicotine treatment of obsessive-compulsive disorder," Prog Neuropsychopharmacol Psychiatry, 2004, vol. 28, p. 1195-1199.

Raventos et al., Application and Possibilities of Supercritical CO2 Extraction in Food Processing Industry: An Overview, Food Science Tech, Int. (2002), vol. 8 (5) pp. 269-284.

Remington's "Remington's Pharmaceutical Science $17^{th}$ Edition." Gannaro, A. (Ed.) pp. 37, 1517-1518. 1985.

Seedher et al. International Journal of Biological Chemistry 1 (3): 162-167 (year 2007).

* cited by examiner

EDIBLE PRODUCT COMPRISING RECONSTITUTED PLANT MATERIAL

RELATED APPLICATIONS

The present application is based upon and claims priority to U.S. patent application Ser. No. 14/448,560 filed on Jul. 31, 2014, which is based upon and claims priority to U.S. Provisional Patent Application Ser. No. 61/861,541 filed on Aug. 2, 2013, both of which are hereby incorporated by reference in their entirety.

FIELD OF THE INVENTION

The present invention relates to an edible product, which comprises a fibrous plant product and a plant extract applied thereto. Further, the invention relates to a corresponding method for producing said edible product and its use in at least one of food, food supplement, medicinal, cosmetic, well-being, nutraceutical or phytotherapeutical applications. The plants used may be all plants comprising one or more substances of interest for an edible product.

BACKGROUND OF THE INVENTION

Today, materials originating from a plant are used in many applications. Such materials are consumed, e.g. as food, food supplement, medicine, for cosmetic reasons or simply for pleasure (taste, color, shape). Native or processed plants can be consumed in different forms, e.g. fresh, dehydrated, cooked, fermented or concentrated (extracts). It is known that food quality has a major impact on health and that plant based materials provide many essential nutrients. It is, for instance, recommended to eat five fruits and vegetables a day to receive a sufficient amount of essential substances such as proteins, sugars, lipids, amino acids, vitamins, polyphenols and aromatic derivates, as well as soluble and insoluble fibers.

People tend to complement or even substitute direct vegetal product consumption (vegetals in their original form) by plant-based material in form of pills, capsules, gums, drops, powders or the like to receive sufficient essential substances. Plant-based material is consumed not only as food supplement but also as nutraceutics, for beauty (e.g. anti-aging), health or traditional medicine/phytotherapy.

Nature is a source of medicinal products for millennia, with many useful drugs developed from plant sources. However, the quality and concentration of substances and functionality, e.g. color, taste or humidity of plants, varies depending on the origin of species seeds), the geographic localization, seasonality, the nature of the soil, growing conditions, harvest date, etc. Further, natural plants can comprise undesired substances or be contaminated, e.g. with bacterial loads, pesticides, heavy metals, mycotoxins and toxic substances. Still further, the desired substances from a natural plant can in many cases not be easily extracted during digestion, e.g. the lycopene trapped in the skin of tomatoes.

There is still a need to improve products originating from plant materials, e.g., for nutraceutical or phytotherapeutical or food supplement use, in particular, it is desirable to control the amount of substances originating from plant materials as well as conditions and time needed to achieve a desired effect.

SUMMARY OF THE INVENTION

The invention relates to an edible product comprising plant materials as raw materials. In particular, the edible product may comprise a fibrous plant product and a plant extract. The fibrous plant product may comprise solid parts of a plant and the plant extract may comprise substances extracted from a plant. The fibrous plant product may form a layer on which the plant extract is applied to. The plant extract can form a second layer or at least partially enter or penetrate into the fibrous plant product. Alternatively, the fibrous plant product can have any shape like pieces, sheets or powder and the plant extract can be applied likewise to the fibrous plant product. According to the invention it is possible to first separate substances from one or more plants and combine one or more of the remaining or separated substances subsequently.

In the easiest case one plant is separated into a plant extract and a fibrous plant product. Subsequently the fibrous plant product and the plant extract are combined to obtain a reconstructed or reconstituted version of the original plant with improved properties. For example, certain substances of the original plant may be easily water-soluble and others not. In this way one can accelerate or even control the release or extraction rate of substances. Also, there can be higher concentrations of certain or all substances as compared to the natural plant.

The fibrous plant product may have at least partially fibrous properties and can comprise substances from one or more specific parts of one or more plants, e.g. a blend of different plants. Also the plant extract can comprises substances from one or more specific parts of one or more plants, e.g. a blend of different plants. Certain substances can be present only in certain parts of a plant, e.g. in one or more of the root, stem, trunk, caulis, leaf, lamina, fruit, flower, seed or bark of a plant. The plant extract may be soluble, e.g. water-soluble, or dispersible.

The plant extract may comprise one or more substances from one or more types of plants of the fibrous plant product. In other words, the plant(s) used as raw material(s) for the fibrous plant product and the plant extract may at least partially be the same.

The plant can be selected from one or more of herbs, medicinal plants, tea, vegetables and/or spices. Examples of plants that are useful in accordance with the present invention are provided in the list shown below. The plant can also be selected from one or more plants containing anthocyanins or carotinoids, or flavonoids. Basically every plant having one or more desired substances for an edible product can be used, e.g. for food, food supplement, medicinal, cosmetic, well-being, nutraceutical or phytotherapeutical applications. Also, any combination of two or more plants can be used.

The product may comprise a layer of fibrous plant product on which a layer of plant extract is formed. Also, the plant extract can partially or entirely penetrate into the fibrous plant product. Also, a multi-layer product with two or more layers of plant extract can be provided, each layer comprising certain substance(s) to provide a certain effect. Optionally, the layers in the multi-layer product can at least partially penetrate into each other. The plant extract can be applied to the fibrous plant product as a fluid or a gel or a slurry or a powder.

The fibrous plant product may comprise at least about 30% or at least about 40% or at least about 50% or at least about 60% or at least about 70% or at least about 80% or at least about 90% or about 100% by weight of fibrous plant product from one plant. Similarly, the plant extract may comprises at least about 30% or at least about 40% or at least about 50% or at least about 60% or at least about 70% or at least about 80% or at least about 90% or about 100% by weight of plant extract from one plant.

Depending on the intended use, the edible product can be a sheet, e.g. a paper like sheet, or a powder or a cream or a slurry or a paste or a foam or a liquid or a tablet or a pellet or a granule. The edible product can be substantially dry, but can optionally be rehydrated, e.g. before use. For example, for use in a food application a dry powder may be rehydrated with water or other liquids or solvents to obtain an edible composition, e.g. a soup. Also, should the edible product be stored or further processed, e.g. finalized or pre-finalized for a specific application, it can be in form of a powder or a sheet for storage or transportation to the finalization process.

The edible product can be one or more of a food, food supplement, medicine, cosmetic, nutraceutical or phytotherapeutic. In the context of the invention a food supplement may not only comprise minerals, vitamins, etc. but may further comprise products for altering the taste or mouthfeel of a food, e.g. spices. Also, the edible product can be used in a method for treating a disease or disorder. Further, the invention also relates to a kit of parts comprising the edible product according to the invention.

The edible product can be produced, at least partially, from certain plants with high level of insoluble fibers. Insoluble fiber is found in the skins of vegetables and fruit and the bran portion of whole grains. Insoluble fiber helps promote regularity and a healthy digestive system. Insoluble fibers are considered gut-healthy fiber because they have a laxative effect and add bulk to the diet, helping prevent constipation. These fibers do not dissolve in water, so they pass through the gastrointestinal tract relatively intact, and speed up the passage of food and waste through your gut. Natural insoluble fibers are mainly found in whole grains and vegetables: whole wheat, whole grains, wheat bran, corn bran, seeds, nuts, barley, couscous, brown rice, bulgur, zucchini, celery, broccoli, cabbage, onions, tomatoes, carrots, cucumbers, green beans, dark leafy vegetables, raisins, grapes, fruit, and root vegetable skins.

The edible product according to the invention can be used for one or more of a food, food supplement, medicinal, cosmetic, well-being, nutraceutical or phytotherapeutical application.

The invention also relates to a method for producing an edible product according to the invention. The method may comprise the steps of:
a) extracting one or more substances of at least one plant to obtain a plant extract;
b) separating the plant extract from the at least partially fibrous residue;
c) optionally refining the residue;
d) preparing a sheet like product from at least a part of the residue;
e) optionally concentrating or purifying or aromatizing the plant extract;
f) applying the plant extract of step b) or e) to the sheet of step d); and
g) optionally drying the product of step f)

It is also possible to select one or more substances or parts from the residue before a product is prepared in step d). Step e) optionally also comprises the selection of certain substances and the filtering of undesired substances. The selection of plants is similar to the respective discussion relating to the product.

In step a) a solvent can be used to extract the one or more substances. A solvent can be any known solvent, such as a polar protic, apolar protic, polar aprotic, apolar aprotic solvent. Also a combination of solvents can be used. The one or more solvents can be determined based on the plant(s) to be processed and the substance(s) to be extracted. Alternatively or in addition to a solvent, extracting the one or more substances can be achieved by mechanical force. To extract substance(s) via mechanical force the plant(s) can be pressed by any known mechanical press or by altering the ambient pressure. Depending on the plant(s) and the substance(s) to be extracted even a simple filtering can be used alone or in addition to solvent(s) or mechanical force as some plants, e.g. after cutting, liberate substances, e.g. in form of liquids. Other filtering means can be used in combination with mechanical vibration, e.g. to separate solid substances such as pollen, from a plant.

The extracting step can be performed using components of a single plant or of a blend of plants. Also, as explained in combination with the product, one or more specific parts of plants can be used.

The at least partially fibrous residue can be mixed with an at least partially fibrous part of at least one further plant prior to preparing the sheet. In this way substances from different origin and with different properties, e.g. mechanical or pharmaceutical, can be mixed together to obtain desired product properties. Also, the at least partially fibrous residue can be mixed with a stabilizer prior to preparing the sheet. For example, the fibrous residue can be mixed with synthetic and/or natural fibers to obtain certain mechanical properties, wherein the fibers are preferably non soluble and/or are approved by food laws.

The plant extract of step b) or e) can be mixed with a plant extract of at least one further plant prior to applying the plant extract to the sheet. Also, the plant extract of step b) or e) can be mixed with a texturing agent prior to applying the plant extract to the sheet. Texturing agents, e.g. emulsifiers or stabilizers or phosphates or dough conditioners, can be used to add or modify the overall texture or mouthfeel of products. Soluble fibers can also be added to the plant extract to modify dietary properties. Soluble fibers attract water and may form a gel, which slows down digestion. Soluble fiber delays the emptying of stomach and makes feel full, which helps control weight. Slower stomach emptying may also affect blood sugar levels and have a beneficial effect on insulin sensitivity, which may help control diabetes. Soluble fibers can also help lower LDL ("bad") blood cholesterol by interfering with the absorption of dietary cholesterol. Exemplary sources of soluble fibers are: oatmeal, oat cereal, lentils, apples, oranges, pears, oat bran, strawberries, nuts, flaxseeds, beans, dried peas, blueberries, psyllium, cucumbers, celery, and carrots.

The method may further comprise the step of adding ingredients or removing ingredients, e.g. undesired compounds or impurities, from the plant extract prior to applying the plant extract of step b) or step e) to the sheet of step d). Similarly the method may further comprise the step of adding or removing ingredients from the at least partially fibrous residue prior to applying the plant extract of step b) or step e) to the sheet of step d).

The composition of step g) can be further processed to obtain regularly or irregularly shaped forms or a powder or a cream or a slurry or a paste or a foam or a liquid or a pellet or a granule.

In case a product contains a liquid content, e.g. a paste, a certain amount or substantially the entire plant extract may be solved or extracted from the fibrous plant product or respective pieces of fibrous plant product. In other words, further processing the composition of step g) by adding a fluid may change the appearance but the advantages of the reconstituted product according to the invention remain.

The method may further comprise the step of processing the sheet like product to obtain a powder or a paste or a cream or a slurry. Exemplary processing steps may comprise cutting or grinding. The powder may be further processed, e.g. to obtain a paste or cream or slurry. The latter step may be accomplished by adding a fluid to the powder. As explained, even if some or substantially all substances are released from the fibrous plant product, the product according to the invention still provides all advantages as all substances are still present, e.g. in the paste.

According to the invention the edible product can be a fiber-web comprising from about 5% to about 100% (w/w), preferably at least about 10%, at least about 20%, at least about 30%, at least about 40%, at least about 50%, at least about 60%, at least about 70%, at least about 80%, at least about 90%, or about 100%, fibers of herbs, medicinal plants, tea, vegetables and/or spices. The fiber-web may further comprise (i) fibers of the herbs, medicinal plants, tea, vegetables and/or spices, and (ii) synthetic and/or natural fibers such as cellulosic fibers in a ratio of for example: 20/80 (w/w), 30/70 (w/w), 40/60 (w/w), 50/50 (w/w), 60/40 (w/w), 70/30 (w/w) or 80/20 (w/w). In another embodiment of the invention, the fiber-web of the present invention is obtainable by the method disclosed herein, namely as an intermediate product in step d) of the said method.

The fiber-web of the invention may further comprise a coating or an impregnation with the plant extract of said herbs, medicinal plants, tea, vegetables and/or spices. The fiber-web of the present invention may be obtainable by the method disclosed herein, namely as the end product in step g) of said method.

Further, the invention relates to an edible packing material comprising the fiber-web referred to herein, which is either impregnated with the plant extract of said herbs, medicinal plants, tea, vegetables and/or spices or which is not impregnated.

The basic idea of the invention is to process one or more plants to obtain an at least partially fibrous residue and a plant extract. Both the fibrous residue and the plant extract can be processed and finally combined to obtain a reconstituted plant product, the properties of which can be controlled depending on the amount and type of substances used. Also other materials not originating from a plant can be added to alter the properties of the resulting product, e.g. to obtain certain mechanical properties or to add a flavor or to improve control of the releasing rate of all or certain substances.

The edible product can be consumed, e.g. by eating, drinking, swallowing, gargling, sucking or chewing.

DETAILED DESCRIPTION OF THE INVENTION

Figure 1:
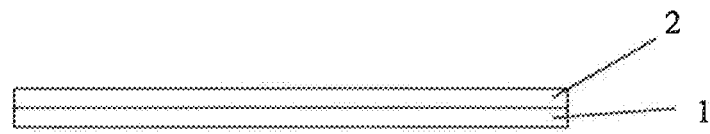
FIG. 1 is a schematic cross sectional view of one exemplary edible product of the invention.

FIG. 1 shows a schematic cross sectional view of an edible product, e.g. a chew gum, according to the invention. The first layer 1 comprises a fibrous plant product and the second layer 2 comprises a plant extract. The first layer may have a thickness of 100 µm to 0.5 cm, preferably 0.2 mm to 5 mm. Instead of having two substantially separate layers, the plant extract can partially or entirely enter or penetrate into the fibrous plant product. The first layer 1 can have a porous structure to facilitate that the plant extract enters into the fibrous plant product. Also, the fibrous plant product can be small pieces of any shape or a paste or a powder and the plant extract can be applied to the plant product.

The product according to the invention may comprise two, three, four, five or more layers, e.g. a first layer 1 comprising a fibrous plant product, a second layer 2 comprising a plant extract with first substance(s), a third layer comprising a plant extract with second substance(s), etc. Each layer may comprise different substances(s) offering a specific effect. Also, additional layers or respective substances in the existing layers can be provided for controlling the sequence and/or amount and/or speed substances are released from the product.

One or both of the plant extract and the fibrous plant product may further comprise a matrix of a texturizing agent, such as a non crosslinked hydrocolloid polymer of natural or synthetic origin, preferably of natural origin. The texturizing agent can be selected from at least one of:

natural agents of plant origin such as carob gum, guar gum, pectins, alginates, carrageenans, agar-agar, gum arabic and cellulose;

of microbial origin such as xanthan gum natural agents, gellan gum, hyaluronic acid and dextran;

animal origin, such as gelatin, collagen and chitosan natural agents;

the mineral agents, such as clays and silicas and synthetic polymers such as polyacrylic and polyacrylamide agents.

The invention can be used in many areas such as for food, food supplement, medicinal, cosmetic, well-being, nutraceutical or phytotherapeutical applications. The plants mentioned in connection with a specific application may also be utilized in connection with other applications.

The reason for the improved properties of the edible product is due to the processing of the raw material(s). According to the invention a controlled amount of selected substances can be placed on the edible product, i.e. in the fibrous plant product or the plant extract. If desired, one plant can substantially be reconstituted or reconstructed so that the final product comprises many or substantially all substances of the raw material. The reconstructed product is advantageous in comparison to the original plant, as the substances from the reconstructed product can be released in a controlled way, e.g. faster than from the natural plant. In addition, it may be desired to mix other substances from other plants or synthetical substances into the edible product to alter its mechanical or other properties. Likewise it can be desired to separate certain undesired substances, e.g. pesticides, metals, polyphenols or substances naturally contained in the plant. The edible product according to the invention can be used as a spice or condiment or flavor to supplement or alter the ingredients of a food, e.g. to improve one or more of taste, texture or mouthfeel, or to add useful substances such as minerals or vitamins. The edible product can be designed to melt or dissolve in part or completely once it comes in contact with a solvent.

For example, the edible product can be a stock cube or a paper like sheet or can be small pieces or a powder. The edible product can be added into a hot, warm or cold food or a solvent such as water, e.g. to prepare a soup or sauce or dressing. Substances from the edible product are infused or released into the solvent or food and the edible product can dissolve in part or entirely. In case the edible product dissolves entirely in the food, like a stock cube, the plant extract as well as the fibrous plant product remain in the food. On the other hand, the edible product might only release certain substances, e.g. the substances contained in the plant extract and/or a part of substances of the fibrous plant product. In the latter case the remaining substances, i.e. what is not dissolved in the food, may be in a form to be separated from the food, e.g. in one piece.

The edible product can be for direct consumption, e.g. by eating, drinking, swallowing, gargling, sucking or chewing. The edible product can be a sweet, a candy, a chew gum or a sheet like paper. Depending on the purpose of the edible product, certain substances may be released once the product comes into contact with saliva, i.e. in the mouth. Other substances may remain in the product and only be released in other digestion steps. In this way it can be controlled where the respective substance(s) shall unfold its effect.

The edible product can comprise substantially all substances needed by an animal or a human being to survive. In this way the edible product can be used as alternative to normal food in cases where no or not sufficient food is available or potentially contaminated.

The edible product can be a food supplement to ensure a certain daily supply of substances such as proteins, sugars, lipids, amino acids, vitamins, polyphenols and aromatic derivates, as well as soluble and insoluble fibers.

The edible product can be used for making a beverage or a soup. Also, the edible product can be used for providing a herbal, vegetable and/or spice composition. The edible product is a plant-based composition or product which is also referred to as plant composition or extraction product.

Hereinafter, the aforementioned product or composition is often referred to as "composition(s) or product(s) of the invention", "composition(s)" or "products". The herbal, vegetable and/or spice composition is also referred to as "mixture of herbs and spices" or "herbal extraction". These terms are used interchangeably and are not intended to limit the invention.

As used herein, the term "plant" likewise refers to any organism of the kingdom Plantae and includes plants described as grains, fruits and vegetables as well as plant parts, such as root, stem, trunk; caulis, leaf, lamina, fruit, flower, seed or bark.

In the products of the invention, the plant is for example selected from the group consisting of herbs, medicinal plants, tea, vegetables and/or spices, including mixtures thereof, such as mixtures of herbs and vegetables, or herbs and spices.

As used herein, a spice is a (either fresh or dried) seed, fruit, root, bark, or vegetative substance primarily used for flavoring, coloring or preserving food. As used herein, herbs are any plants used for flavoring, food, medicine, or perfume. Culinary use typically distinguishes herbs as referring to the leafy green parts of a plant (either fresh or dried), from a "spice", a product from another part of the plant (usually dried), including seeds, berries, bark, roots and fruits.

Examples of plants that are useful in accordance with the present invention are provided in the list shown below.

The edible product can be a herbal and/or vegetable composition, e.g., for culinary use or for use in cooking, i.e. as a herb and spice mixture.

The invention further relates to a method for producing the edible product. For example, the method comprises the steps of:

a) extracting one or more substances of at least one plant to obtain a plant extract;

b) separating the plant extract from the at least partially fibrous residue;

c) optionally refining the residue;

d) preparing a sheet like product from the residue, optionally a sheet like product;

e) optionally concentrating or purifying or aromatizing the plant extract;

f) applying the plant extract of step b) or e) to the sheet of step d); and g) optionally drying the product of step f)

In one embodiment of the invention, one or more plant components (plant material or plant funish) such as, for example, stems, scraps, leaves, fines, dust and/or shorts, are initially mixed with a solvent (e.g., water and/or other compounds) at elevated temperatures. For example, various solvents that are water-miscible, such as alcohols (e.g., ethanol), can be combined with water to form an aqueous solvent. The water content of the aqueous solvent can, in some instances, be greater than 50% by weight of the solvent. In one embodiment, the water content is at least about 70%, or at least about 80%, or at least about 90% or about 100% by weight of the solvent. Deionized water, distilled water or tap water may be employed. The amount of the solvent in the suspension can vary widely, but is generally added in an amount from about 75% to about 99% by weight of the suspension. However, the amount of solvent can vary with the nature of the solvent, the temperature at which the extraction is to be carried out, and the type of plant components.

After forming the solvent/plant furnish mixture, some or all of a soluble extracts fraction of the furnish mixture may be optionally separated (e.g., extracted) from the mixture. If desired, the aqueous solvent/plant furnish mixture can be agitated during extraction by stirring, shaking or otherwise mixing the mixture in order to increase the rate of extraction. Typically, extraction is carried out for about 0.5 hours to about 6 hours. Moreover, although not required, typical extraction temperatures range from about 10° C. to about 100° C.

Prior to the extraction step an optional grinding or cutting step can be used, in order to shred the plant or plant part and thus to break the plant's cell walls.

Once separated from the insoluble residue fraction of the plant solution, the soluble extracts fraction can optionally be concentrated using any known type of concentrator, such as a vacuum evaporator. In one embodiment, the soluble component may be highly concentrated. Moreover, the concentrated or unconcentrated soluble extracts fraction can be utilized in any manner desired. For example, the soluble extracts fraction can be utilized as a flavoring material or a portion can be added to the insoluble residue fraction.

Once extracted, the insoluble residue fraction can optionally be subjected to one or more mechanical refiners to produce a fibrous pulp. Some examples of suitable refiners can include disc refiners, conical refiners, and the like. The insoluble residue fraction can be utilized in any manner desired. For example, the insoluble residue fraction can be used as a flavoring material, used to produce a composition of the invention, which is herein also referred to as reconstituted plant material.

To produce a product of the invention, the insoluble residue fraction can be transferred to a papermaking station. The papermaking station includes a forming apparatus, which may include, for example, a forming wire, gravity drain, suction drain, felt press, Yankee dryer, drum dryers, etc. In general, the insoluble residue fraction may be in the form of a pulp. In the forming apparatus, the pulp is laid onto a wire belt forming a sheet-like shape. Excess water is removed from the sheet using gravity drains, suction drains, presses, and dryers. Thereafter, if desired, a portion of the soluble extracts fraction may be reapplied to the insoluble residue fraction. When the insoluble residue fraction is recombined with the soluble extracts fraction, the resulting plant product is generally referred to as "reconstituted plant material".

Reconstituted plant material can generally be formed in a variety of ways. For instance, in one embodiment, band casting can be utilized to form the reconstituted plant material. Band casting typically employs a slurry of finely divided plant parts mixed with a binder such as gum arabic, guar gum, alginate, xanthan, cellulose and cellulose derivatives (such as carboxy methyl cellulose (CMC), hydroxypropyl methyl cellulose (HPMC)), pectines or starch that is coated onto a steel band and then dried. In one embodiment, the method is performed according to a process similar to the conventional tobacco reconstitution process, which is for example described in U.S. Pat. Nos. 3,353,541; 3,420,241; 3,386,449; 3,760,815; and 4,674,519; which are incorporated herein in their entirety by reference thereto. The method for producing the products of the invention can also be performed by a papermaking process, in order to reconstitute any plant components (such as stems, scraps, leaves, fines, dust and/or shorts) into a paper-like product. Some examples of such processes are described in U.S. Pat. Nos. 3,428,053; 3,415,253; 3,561,451; 3,467,109; 3,483,874; 3,860,012; 3,847,164; 4,182,349; 5,715,844; 5,724,998; and 5,765,570; which are also incorporated herein in their entirety by reference thereto for all purposes. For example, the formation of the products of the invention using papermaking techniques can involve the steps of mixing herbs, medicinal plants, tea, vegetables and/or spices with water, extracting the soluble ingredients therefrom, concentrating the soluble ingredients, refining the herbs, medicinal plants, tea, vegetables and/or spices, forming a web, reapplying the concentrated soluble ingredients, drying, and threshing.

In the method of the invention, more specifically with respect to the non-soluble portion (solid plant particles) used in providing the non-impregnated fiber web of the invention, i.e. the sheet-like product in step d), the plant is not tobacco, wood pulp, cotton, textiles, jute flax, Indian hemp, hemp, hoopvine, kenaf, nettles, ramie, abacá, bamboo fiber, banana (especially banana bark), bowstring hemp, coir (fiber from the coconut shell), esparto, henequen, kapok, milkweed, papaya, phormium ("New Zealand Flax"), sisal, raffia, bagasse, pina, aibika or yucca. However, a mixture of a plant mentioned herein in connection with the present invention with any of the aforementioned plants may be utilized. Further to the foregoing listed materials also others materials can be added to improve product physical characteristics, for example cellulose derivatives such as methylcellulose, carboxymethyl cellulose (CMC), hydroxypropyl methyl cellulose (HPMC), starch and starch derivatives such as oxidatively degraded starch, polysaccharides (and their derivatives) such as pectines, gelatins, guar gum, agar, alginates, carrageenans, or synthetic fibers such as the ones made of vinyl chloride or vinyl acetate, polyethylene, polypropylene, polyesters.

Once extracted, the insoluble, solids portion can optionally be subjected to one or more mechanical refiners to produce a fibrous pulp. Some examples of suitable refiners can include disc refiners, conical refiners, and the like, well known to a skilled person. The pulp from the refiner can then be transferred to a papermaking station that includes a forming apparatus, which may include, for example, a forming wire, gravity drain, suction drain, felt press, Yankee dryer, drum dryers, etc. In such a forming apparatus, the pulp is laid onto a wire belt forming a sheet-like shape and excess water is removed by the gravity drain and suction drain and presses. Once separated from the insoluble portion of the plant solution (plant extract), the soluble portion can optionally be concentrated using any known type of concentrator, such as a vacuum evaporator.

In some embodiments of the invention, a wet strength agent may be added to the fibrous portion in order to reduce potential degradation of the reconstituted material when it is brought into contact with a liquid (e.g. water), such as upon infusion in water. Any suitable wet strength agent preferably selected for food applications may be used such as polyamide-epichlorohydrin resins, polyamine-epichlorohydrin resins, poly(aminoamide)-epichlorohydrin resins, urea-formaldehyde resins; melamine-formaldehyde resins; alkyl ketene dimer; alkyl succinic anhydride; polyvinylamines; oxidized polysaccharides (such as oxidatively degraded starch); glyoxalated polyacrylamide resins; polyimines such as polyethyleneimine. Wet strength agents are well known to the skilled person and described in Ingredients Standards, such as BFR (Bundesinstitut für Risikobewertung) XXXVI and BFR XXXVI/1 or FDA (Food & Drug Administration) 21 CFR 176.170, FDA 21 CFR 176.110, FDA 21 CFR 176.120, FDA 21 CFR 176.1180. The wet strength agent is for example used in an amount of about 0.1% w/w to about 20% w/w, preferably of about 1% w/w to about 10% w/w, more preferably of about 5% w/w. The wet strength agent is preferably added to the fibrous portion when or before making the sheet-like product (see step d) above).

In one embodiment, the water used for extraction is hot water, preferably of about 30° C. to 100° C., about 40° C. to 90° C., or about 50° C. to 80° C., or more preferably of about 70° C.

In one embodiment, the coating ratio of solubles portion onto the fiber web is about 5% to 80% (w/w), about 10% to 70% (w/w), or more preferably between about 20% and 50% (w/w). In some embodiments, the coating ratio or soluble portion that is added back to the base web (fiber web) is similar to the portion of soluble material contained in and extracted from the original plant (so called "standard level").

In one embodiment, the base weight of the final product is about 20 to about 200 g/m$^2$ (dry has more preferably about 90 g/m$^2$ to about 120 g/m$^2$.

The extraction time depends on the herbs, medicinal plants, tea, vegetables and/or spices subjected to the extraction process. In one embodiment of the invention, the extraction time is about 15 to 60 minutes, preferably 45 minutes.

In one embodiment of the method of the invention, the extracting step is performed using components of a blend of plants, in another embodiment, extracting step is performed using components of a single plant.

Extraction may also be performed by means other than using hot water, namely by extraction with supercritical gases, such as carbon dioxide, or by using, for example, ethanol, hexane, acetone, R134a (1,1,1,2-tetrafluoroethane), carbon dioxide and hydrofluorocarbons. In one embodiment, the extraction can be carried out by using at least one solvent at room temperature and under atmospheric pressure. Extraction may also be performed by using a mixture of different solvents. In another embodiment, extraction may be performed using at least one solvent, such as for example R134a or carbon dioxide, at different temperatures and at different pressures and different states (liquid or gaseous), For example, extraction may be performed using solvents in a liquid state (such as solvent that are volatile or non-volatile at room temperature), in a subcritical state (such as water at a temperature above 100° C. and a pressure above 1 bar), or in a supercritical state (such as carbon dioxide at a temperature above 31° C. and a pressure above 73 bar).

Certain plants may require specific extraction conditions (time, temperature, solid/liquid ratio) due to the ingredients contained therein, which may be temperature sensitive or must not be subjected to certain extraction conditions. For example, extraction of lycopene from tomatoes must be performed by using specific enzymes to liberate the product from tomatoes cells. In connection with the present invention, processing aids may be used to improve extraction, such as pH modifiers (such as, for example, NaOH or organic acids), microwaves, pressure, ultrasound, enzymes such as for example proteases, amylases, cellulose, and/or pectinases. Whenever reference is made herein to "extraction", the term includes the aforementioned alternative extraction means. The extraction used in connection with the present invention can be performed in a continuous or discontinuous matter. The extraction conditions are well known to the skilled artisan and described in standard text books, such as Handbook of Separation Techniques for Chemical Engineers, Third Edition (March 1997), Philip A. Schweitzer, McGraw-Hill Inc.

In one embodiment, the extraction and/or pressing may be performed using at least a portion of the plant material, fresh, frozen or dried, selected from one or more of root, stem, trunk, caulis, leaf, lamina, fruit, flower, seed of bark.

Separation of the soluble portion (plant extract) from the non-soluble portion (solid plant particles) can be performed by separating the liquid phase from the solid phase, such as by filtration, with or without pressure, by centrifugation or other methods commonly used in the laboratory and well-known to the skilled person.

In one embodiment of the method where a mixture or blend of plants is used, the non-soluble portion of the plant is mixed with the non-soluble portion of at least one further plant prior to preparing the sheet.

Certain embodiments of the method of the invention use the soluble portion of step b) or concentrated soluble portion of step e), which is mixed with the soluble portion or concentrated soluble portion of at least one further plant prior to applying the soluble portion or concentrated soluble portion to the sheet.

For certain applications it is desirable to adjust the composition by adding or removing ingredients or components to or from the plant extract and/or the non-soluble plant particles prior to producing the final product of the invention. Such adjustment may be performed to modify/improve chemical, physical and/or sensory characteristics of the finished product. The invention thus encompasses methods, further comprising the step of adding or removing ingredients from the soluble portion (plant extract) and/or from the non-soluble portion (solid plant particles) prior to applying the soluble portion of step b) or concentrated soluble portion of step e) to the sheet of step d).

In some embodiments, the sheet or sheet-like product which is obtained in step g) is a web or fiber-web. The sheet-like product or web may be used in different sizes and shapes. In some cases, the composition of step g) is further cut or broken into small regularly or irregularly shaped forms or processed to obtain a powder, e.g. by grinding. In addition to cutting or breaking the sheet or fibrous web to a desired size and/or shape, it may be dried to the desired final moisture content.

Also, product can be supplied to food industries in sheet or bobbin forms which can be later used as an ingredient for food manufacturing. It is indeed a very convenient option to store, manipulate and adjust dosage of herbs or spices.

One possible grinding method is cryogenic grinding. Cryogenic grinding, also known as freezer milling, freezer grinding, or cryomilling, is the act of cooling or chilling a material and then reducing it into a small particle size. Heat and oxidation reactions usually occur on the material with standard grinding technologies, at room temperature. Thanks to cryogenic grinding, enzymes, vitamins and many other active molecules are preserved from such reactions. This technology is used to prepare medicinal plant powders.

The product according to the invention may also be pelletized, e.g. to produce tablets or granule. Pelletizing is the process of compressing or molding a material into the shape of a pellet. Ingredients are normally first hammered to reduce the particle size of the ingredients. Ingredients are then batched, and then combined and mixed thoroughly by a feed mixer. Once the feed has been prepared to this stage the feed is ready to be pelletized. Pelletizing is done in a pellet mill, where feed is normally conditioned and thermally treated in the fitted conditioners of a pellet mill. The feed is then pushed through the holes and a pellet die and exit the pellet mill as pelleted feed. After pelleting the pellets are cooled with a cooler to bring the temperature of the feed down. Other post pelleting applications include post-pelleting conditioning, sorting via a screen and maybe coating if required.

In accordance with the present invention the plant is selected from the group consisting of herbs, medicinal plants, tea, vegetables and/or spices, including mixtures thereof. The following list of plants (such as herbs, medicinal plants, tea, vegetables and/or spices) referred to herein provides an overview of exemplary plants that can be used in connection with the invention. It is noted that the list is not limiting, as any plant having one or more substances desired for use in an edible product can be utilized. Also, two or more plants may be used together in a product according to the invention. Examples of plants that are useful in accordance with the present invention are:

*Abelmoschus* spp., *Abies* spp., *Abroma augusta, Acacia* spp., *Acalypha indica, Acanthus mollis, Acer* spp., *Achillea* spp., *Achyranthes bidentata, Acmella oleracea, Acorus calamus, Actaea* spp., *Actinidia* spp., *Adansonia digitata, Adiantum* spp., *Adoxa moschatellina, Aegopodium podagraria, Aesculus* spp., *Aframomum* spp., *Agathosma* spp., *Agave* spp., *Agrimonia* spp., *Ajuga* spp., *Alaria esculenta, Albizia* spp., *Alcea rosea, Alchemilla vulgaris, Aletris farinosa, Alisma* spp., *Alliaria petiolata, Allium* spp., *Alnus* spp., *Aloe* spp., *Aloysia citriodora, Alpinia* spp., *Althaea officinalis, Amaranthus* spp., *Ammi visnaga, Amomum villosum, Amorphophallus konjac, Amyris balsamifera, Anacardium occidentale, Ananas comosus, Andrographis paniculata, Anemarrhena asphodeloides, Angelica* spp., *Angostura trifoliata, Aniba rosaeodora, Annona* spp., *Anogeissus latifolia, Anredera baselloides, Antennaria dioica, Anthemis* spp., *Anthriscus* spp., *Anthyllis vulneraria, Antirrhinum majus, Aphanes arvensis, Apium graveolens, Arachis hypogaea, Aralia* spp., *Arbutus unedo, Arctium* spp., *Argania spinosa, Armoracia rusticana, Artemisia* spp., *Artocarpus altilis, Ascophyllum nodosum, Asimina triloba, Aspalathus linearis, Asparagus* spp., *Asplenium* spp., *Astracantha* spp., *Astragalus* spp., *Astrantia major, Athamanta macedonica, Atractylodes* spp., *Avena* spp., *Averrhoa carambola, Baccharis genistelloides, Bacopa monnieri, Bactris gasipaes, Balanites aegyptiaca, Ballota* spp., *Bambusa* spp., *Barbarea* spp., *Bellis perennis, Berberis* spp., *Bergenia crassifolia, Bertholletia excelsa, Beta vulgaris, Betula* spp., *Bixa orellana, Blainvillea acmella, Borago officinalis, Boronia megastigma, Boswellia* spp., *Brassica* spp., *Bupleurum* spp., *Bursera tomentosa, Caesalpinia bonduc, Cakile maritima, Calendula* spp., *Calluna vulgaris, Calophyllum inophyllum, Camelina* spp., *Canarium acutifolium, Canavalia ensiformis, Cannabis sativa, Capparis spinosa, Capsella bursa-pastoris, Carex arenaria, Carica papaya, Carissa carandas, Carlina* spp., *Carpinus betulas, Carthamus* spp., *Carum carvi, Cassia* spp., *Castanea sativa, Catalpa bignonioides, Ceanothus americanus, Cecropia peltata, Cedrus libani, Ceiba pentandra, Centaurea* spp., *Centaurium erythraea, Centella asiatica, Centranthus ruber, Cerasus* spp., *Ceratonia siliqua, Cercis siliquastrum, Ceterach officinarum, Cetraria islandica, Chaenomeles speciosa, Chamaemelum nobile, Chamaecrista nomame, Chelone glabra, Chenopodium* spp., *Chimaphila umbellata, Chiococca alba, Chionanthus virginicus, Chlorella vulgaris, Chondrus crispus, Chrysanthellum* spp., *Chrysophyllum cainito, Chrysopogon zizanioides, Cichorium* spp., *Cinchona* spp., *Cinnamomum* spp., *Cistanche salsa, Cistus* spp., *Citrullus lanatus, Citrus* spp., *Cladonia rangiferina, Clematis* spp., *Clinopodium vulgare, Clitoria ternatea, Cnicus benedictus, Cochlearia officinalis, Cocos nucifera, Codonopsis pilosula, Coffea* spp., *Coix lacryma-jobi, Cola* spp., *Combretum* spp., *Commiphora* spp., *Conyza canadensis, Copaifera langsdorffii, Coptis* spp., *Corallina officinalis Cordia myxa, Coriandrum sativum, Cornus domestica, Cornus* spp., *Corrigiola telephiifolia, Corylus avellana, Corymbia citriodora, Coscinium fenestratum, Cotinus coggygria, Crambe maritima, Crataegus* spp., *Crithmum maritimum, Crocus sativus, Crossostephium chinense, Croton nitens, Cruciata laevipes, Cryptocarya agathophylla, Cucumis* spp., *Cucurbita maxima, Cuminum cyminum, Cupressus sempervirens, Curcuma* spp., *Cuscuta* spp., *Cyamopsis tetragonoloba, Cyathula officinalis, Cyclanthera pedata, Cydonia oblonga, Cymbopogon* spp., *Cynara* spp., *Cyperus rotundus, Cytinus hypocistis, Daemonorops draco, Dahlia pinnata, Daucus carota, Dendranthema grandiflorum, Descurainia sophia, Dianthus caryophyllus, Dimocarpus longan, Dioscorea* spp., *Diospyros* spp., *Diplotaxis tenuifolia, Dipsacus* spp., *Dorstenia contrajerva, Dracocephalum moldavica, Drimys Winteri, Drosera* spp., *Dunaliella salina, Durio zibethinus, Durvillea antartica, Dysphania botrys, Echinacea* spp., *Echium plantagineum, Elaeis guineensis, Elettaria cardamomum, Eleutherococcus senticosus, Elymus repens, Epilobium* spp., *Equisetum* spp., *Erica* spp., *Eriobotrya japonica, Eriodictyon californicum, Erodium cicutarium, Eruca vesicaria, Eryngium campestre, Eschscholtzia, Eucalyptus* spp., *Eucheuma* spp., *Eucommia ulmoides, Eugenia uniflora, Euphrasia* spp., *Euterpe oleracea, Evernia prunastri, Exostema caribaeum, Fabiana imbricata, Fagopyrum esculenturn, Fagus sylvatica., Fallopia* spp., *Ferula assa-foetida, Ficus* spp., *Filipendula* spp., *Foeniculum vulgare, Forsythia suspensa, Fragaria* spp., *Frangula* spp., *Fraxinus* spp., *Fucus* spp., *Fumaria officinalis, Galega officinalis, Galeopsis segetum, Galium* spp., *Garcinia* spp., *Gardenia jasminoides, Gastrodia elata, Gaultheria procumbens, Gelidium* spp., *Gentiana lutea, Geranium* spp., *Geum* spp., *Ginkgo biloba, Glycine max, Glycyrrhiza* spp., *Gossypium herbaceum, Gracilaria gracilis, Griffonia simplicifolia, Grindelia* spp., *Guaiacum* spp., *Guazunma ulmifolia, Gynostemma pentafillum, Gypsophila paniculata, Haematococcus pluvialis, Haematoxylum campechianum, Hamamelis virginiana, Handroanthus impetiginosus, Haplopappus baylahuen, Harpagophytum* spp., *Hebanthe eriantha, Hedeoma pulegioides, Hedera helix, Hedychium coronarium, Helianthus* spp., *Helichrysum* spp., *Heracleum sphondylium, Herniaria* spp., *Hesperis matronalis, Hibiscus sabdariffa, Hieracium pilosella, Hierochloe odorata, Himanthalia elongata, Hippophae rhamnoides, Hizikia fusiformis, Hordeurn vulgare, Houttuynia cordata, Humulus lupulus, Hydrangea arborescens, Hygrophila auriculata, Hymenaea courbaril, Hypericum perforatum Hyssopus officinalis, Ilex paraguariensis, Illicium verurn, Impatiens balsamina, Indigofera tinctoria, Inula* spp., *Ipomoea batatas, Isatis tinctoria, Jasminum* spp., *Jateorhiza palmata, Juglans* spp., *Jumellea fragrans, Juniperus communis, Justicia* spp., *Kaempferia galanga, Kavalama urens, Kickxia spuria, Knautia arvensis, Krameria lappacea, Lactuca* spp., *Lagerstroemia speciosa, Laminaria* spp., *Lamium album, Larix* spp., *Laurus nobilis, Lavandula* spp., *Lawsonia inermis,*

*Ledum palustre, Lens culinaris* Medik, *Leonurus cardiaca, Lepidium* spp., *Leptospermum* spp., *Lespedeza capitata, Leucanthemum vulgare, Levisticum officinale, Lilium brownii, Linaria vulgaris, Lindera aggregata, Linum usitatissimum, Liquidambar styraciflua, Litchi chinensis, Lithothamnion calcareum, Litsea cubeba, Lobaria pulmonaria, Lonicera japonica, Lotus* spp., *Luma chequen, Lycium* spp., *Lycopersicon esculentum, Lycopodium clavatum, Lycopus* spp., *Lysimachia vulgaris, Lythrum salicaria, Macadamia ternifolia, Macrocystis pyrifera, Magnolia* spp., *Malpighia glabra, Malus* spp., *Malva sylvestris, Mammea americana, Mangifera Manihot esculenta, Manilkara zapota, Maranta arundinacea, Marchantia polymorpha, Marrubium vulgare, Marsdenia* spp., *Mastocarpus stellatus, Matricaria chamomilla, Medicago sativa, Melaleuca* spp., *Melilotus* spp., *Melissa officinalis, Melittis melissophyllum, Mentha* spp., *Mentzelia cordifolia, Menyanthes trifoliata, Mesembryanthemum crystallinum, Mespilus germanica, Mikania amara, Mitchella repens, Momordica* spp., *Monarda* spp., *Morinda* spp., *Moringa oleifera, Morus* spp., *Murraya koenigii, Musa* x *paradisiaca, Myrciaria dubia, Myrica gale, Myristica fragrans, Myroxylon* spp., *Myrtus communis, Nardostachys jatamansi, Nasturtium officinale, Nelumbo nucifera, Nepeta* spp., *Nephelium lappaceum, Nigella sativa, Ocimum* spp., *Oenanthe aquatica, Oenothera biennis, Olea* spp., *Ononis* spp., *Onopordon acanthium, Ophioglossum vulgatum, Ophiopogon japonicus, Opopanax chironius, Opuntia ficus-indica, Orchis mascula, Origanum* spp., *Orthosiphon* spp., *Oryza sativa, Oxalis acetosella, Pachira* spp., *Padus avium, Paeonia* spp., *Palmaria palmata, Panax* spp., *Panicum miliaceum, Panzerina lanata, Papaver rhoeas, Parietaria officinalis, Parmelia saxatilis, Parthenium hysterophores, Parthenocissus tricuspidata, Passiflora incarnata, Pastinaca sativa, Paullinia cupana, Pedalium murex, Pelargonium* spp., *Perilla frutescens, Persea americana, Persicaria* spp., *Petiveria alliacea, Petroselinum crispum, Peucedanum ostruthium, Peumus boldus, Phaseolus vulgaris, Phellodendron amurense, Phillyrea latifolia, Phlebodium aureum, Phoenix dactylifera, Photinia melanocarpa, Phyla scaberrima, Phyllanthus* spp., *Phymatolithon calcareum, Physalis* spp., *Picea abies, Picramnia antidesma, Pimenta* spp., *Pimpinella* spp., *Pinus* spp., *Piper* spp., *Pistacia* spp., *Pisum sativum, Plantago* spp., *Platycodon grandiflorus, Plectranthus barbatus, Pogostemon cablin, Polygala* spp., *Polygonatum odoratum, Polygonum aviculare, Populus* spp., *Porphyra umbilicalis, Portulaca oleracea, Potentilla* spp., *Prangos pabularia, Primula* spp., *Protium* spp., *Prunella vulgaris, Prunus* spp., *Psidium* spp., *Pterocarpus* spp., *Pueraria* spp., *Pulmonaria officinalis, Punica granatum, Pyrola rotundifolia, Pyropia tenera, Pyrus communis, Quercus* spp., *Quillaja saponaria, Raphanus* spp., *Raphia farinifera, Rehmannia glutinosa, Rhamnus* spp., *Rheum* spp., *Rhodiola crenulata, Rhus* spp., *Ribes* spp., *Robinia pseudoacacia, Roccella phycopsis, Rosa* spp., *Rosmarinus officinalis, Rubia cordifolia, Rubus* spp., *Rumex* spp., *Ruscus* spp., *Sabatia angularis, Saccharina latissima, Saccharum officinarum, Salix* spp., *Salvia* spp., *Sambucus* spp., *Sanguisorba* spp., *Sanicula elata, Santalum album, Santolina chamaecyparissus, Saponaria officinalis, Saposhnikovia divaricata, Sarcopoterium spinosum, Sargassum fusiforme, Sarracenia purpurea, Satureja* spp., *Saussurea costus, Schinus molle, Schisandra chinensis, Scorzonera hispanica, Scrophularia ningpoensis, Scutellaria* spp., *Secale cereale, Sedum* spp., *Selenicereus grandiflorus, Sempervivum tectorum, Senna* spp., *Sequoiadendron giganteum, Serenoa repens, Sesamum indicum, Seseli tortuosum, Sideritis syriaca, Sigesbeckia orientalis, Silaum silaus, Silybum marianum, Sirnarouba amara, Simmondsia chinensis, Siraitia grosvenorii, Sisymbrium officinale, Sium latifolium, Smilax* spp., *Solanum* spp., *Solidago virgaurea, Sorbus aucuparia, Sorghum bicolor, Spatholobus suberectus, Spergularia rubra, Spinacia oleracea, Spirulina* spp., *Stachys officinalis* spp., *Stellaria media, Stenimacantha carthamoides, Styphnolobium japonicum, Styrax* spp., *Symplocarpus foetidus, Syringa vulgaris, Syzygium* spp., *Tagetes* spp., *Tamarindus indica, Tamarix gallica, Tanacetum* spp., *Taraxacum officinale, Terminalia* spp., *Thalictrum flavum, Theobroma cacao, Thlaspi arvense, Thymus* spp., *Tilia* spp., *Trachyspermum ammi, Tragopogon porrifolius, Tribulus terrestris, Trichina catigua, Trichosanthes kirilowii, Tridax procumbens, Trifolium* spp., *Trigonella* spp., *Trillium erectum, Triticum* spp., *Tropaeolum* spp., *Tsuga Canadensis, Turnera diffusa, Ulmus* spp., *Ulva lactuca, Uncaria* spp., *Undaria pinnatifida, Urtica* spp., *Usnea* spp., *Vaccinium* spp., *Valeriana* spp., *Valerianella locusta, Vanilla planifolia, Veratrum viride, Verbascum* spp., *Verbena officinalis, Veronica* spp., *Viburnum* spp., *Vicia* spp., *Vigna angularis, Viola* spp., *Viscum album, Vitex* spp., *Vitis vinifera, Withania somnifera, Xeranthemum annuum, Yucca* spp., *Zanthoxylum* spp., *Zea mays, Zingiber officinale, Ziziphus jujube.*

In a further embodiment, the invention relates to a fiber-web comprising from about 5% to about 100% (w/w), preferably at least about 10%, at least about 20%, at least about 30%, at least about 40%, at least about 50%, at least about 60%, at least about 70%, at least about 80%, at least about 90%, or about 100%, fibers of herbs, medicinal plants, tea, vegetables and/or spices. In one embodiment, the fiber-web further comprises cellulosic and/or synthetic fibers, and fibers of herbs, medicinal plants, tea, vegetables and/or spices in a ratio of for example: 40/60 (w/w), 50/50 (w/w), 60/40 (w/w), 70/30 (w/w) or 20/80 (w/w). In another embodiment of the invention, the fiber-web of the present invention is obtainable by the method disclosed herein, namely as an intermediate product in step d) of the said method.

The invention further relates to a composition for making a beverage, obtainable by the method of the present invention disclosed herein.

The invention also includes the use of the composition of the invention for making a beverage, or for culinary use or use in cooking, respectively, i.e. as a herb and spice mixture.

Also included is a beverage obtainable by contacting water or another liquid with the composition of the invention.

In one embodiment of the invention, the fiber-web comprises from about 5% to about 100% (w/w), preferably at least about 10%, at least about 20%, at least about 30%, at least about 40%, at least about 50%, at least about 60%, at least about 70%, at least about 80%, at least about 90%, or about 100%, fibers of herbs, medicinal plants, tea, vegetables and/or spices. For certain applications, the fiber-web may further comprise synthetic and/or natural fibers such as cellulosic fibers. In a particular embodiment, the fiber-web comprises fibers of (i) herbs, medicinal plants, and/or tea, vegetables and/or spices and (ii) synthetic and/or natural fibers such as cellulosic fibers in a ratio of 40/60 (w/w), 60/40 (w/w) or 80/20 (yew).

The invention further relates to a fiber-web, obtainable by the method of the invention, namely in step d).

In some embodiments of the invention, the fiber-web further comprises a coating or impregnation with soluble portion (plant extract) of herbs, medicinal plants, tea, vegetables and/or spices.

The coating or impregnation is obtained by various methods known to the skilled person, such as applying to or treating the fiber-web or sheet-like structure with a plant extract, such as in a bath or by special application means, such as sprayers. In addition, various other ingredients, such as flavor or color treatments, can also be applied to the web. If applied with the soluble portion and/or other ingredients, the fibrous sheet material can, in some embodiments, then be dried using, for example, a tunnel dryer, to provide a sheet having a typical moisture content of less than 20% by weight, and particularly from about 9% to about 14% by weight.

The invention thus also relates to an impregnated or coated fiber-web, obtainable by the method of the invention, namely in step g).

According to a further embodiment, the fiber-web of the invention further comprises a coating or an impregnation with the soluble portion (plant extract) of said herbs, medicinal plants, tea, vegetables and/or spices. In another embodiment of the invention, the fiber-web of the present invention is obtainable by the method disclosed herein, namely as the end product in step g) of said method.

The products of the invention enable a more efficient extraction (up to about 100% solubles can be extracted from the plant) in the sense that more solubles can be released than natural plant ingredients for a given weight of material. The products also provide a faster extraction (than with a conventional extraction made from the vegetal material in its natural non converted form). Specifically, the compositions of the invention have improved efficiency, e.g. in boiling water or in non-heated water or water at room temperature.

The process for making the compositions of the invention also allows for specifically adjusting the final composition of the products, such as to remove from the soluble or the non-soluble portion(s) for example foreign matters, components altering taste and/or odor, or caffeine, pesticides, heavy metals, mycotoxins, toxicants and allergenic molecules such as coumarin, farnesol, geraniol, limonene, linalol, safrole, methyleugenol, or by adding to the soluble or the non-soluble portion(s) for example desirable additives, such as sweeteners, sugars, flavors, casings, vitamins, colorants, minerals, taste enhancers.

In another embodiment, the soluble portion in the reconstituted material of the invention can be precisely adjusted (decreased as compared to standard level, at standard level, or increased as compared to standard level). A key benefit is that the level of ingredients in the reconstituted material can be precisely increased to a level higher than in the original natural form, thus allowing for products with a higher concentration of desired substances. The adjustment of ingredients can also guarantee a consistent, standardized level of delivered ingredients to compensate natural variations of substances, i.e. active ingredients, in plants.

Preferably, the method of the invention also allows for reduction of undesired compounds from the material, such as to selectively remove undesired components (natural ingredients, pesticides, impurities or the like). For example, it is possible to remove components from either the soluble portion (plant extract) or from the non-soluble portion (solid plant particles) or both by liquid-liquid extraction, physical adsorption, centrifugation, chromatography, crystallization, decantation, by use of a demister, drying, distillation, electrophoresis, elutriation, evaporation, solid phase or liquid-liquid extraction, flotation, flocculation, filtration (for example using membranes), vapor-liquid separation, and/or sublimation and other means well known to the skilled person, preferably before applying the plant extract to the base web.

In connection with adding ingredients, extracts of different sources and origins, flavors, coloring agents or the like may be used, such as chlorophyll, anthocyans, caramel, caroteinoids. For example, when using tea or herbs it is possible to include L-menthol at various quantities (such as 6% or 15%) in the finished product. Products so obtained have a distinctive taste and aroma of menthol.

The present invention also allows to blend various plants and herbs. In one example, instead of using single plants, such as tea or mint leaves, tea may be replaced by a mixture of, for example, 50% tea and 50% mint leaves (w/w); 50% verbena and 50% mint (w/w); 30% cinnamon and 30% tea and 10% licorice and 10% chamomile and 10% red vine and 10% roobois (w/w); and many other combinations.

The combination of different plant materials through the reconstitution process into a single fiber web impregnated with extracts from different plants (the same plant or blends) offers new taste experiences and additive or synergistic effects. For example, it is known that combinations of certain plant extracts or combinations of certain plant ingredients have additive or synergistic effects, such as, for example, a mixture of hops and valerian extracts for use in treating insomnia and vigilance (Blumenthal and al., J. Herbal Medicine, expanded Commission E monographs, American Botanical Council, Austin, 2000, 394-400), or mixtures of oregano and cranberry extracts for use in treating *H. pylori* infections (Lin et al., Appl. Environ. Microbiol. December 2005, vol. 71, no. 12, 8558-8564), or different mixtures of extracts of *S. baicalensis, D. morifolium, G. uralensis* and *R. rubescens* tested for their additive or synergistic effect in prostate cancer cell lines (Adams et al., Evid Based Complement Alternat Med. 2006 March; 3(1): 117-124).

It has been found that some beverages are particularly less astringent and bitter when prepared from the reconstituted plant material or product of the invention as compared to original material from which the reconstituted plant material or product of the invention was prepared. This is, for example, the case for green tea, which is less astringent and bitter when made from a reconstituted green tea product according to the invention as compared to a conventional infusion of green tea.

The production method also provides for reducing microbiological load of the final products because of the high temperatures during the papermaking process.

The products of the invention provide a light material having a small surface, which allows economic packaging/shipping. For the consumer, the products of the invention are easy to transport and easy to use. Specifically, it has been found that the products of the invention are easily extractable even in cold water. This has particular advantages for consumers in cases where no heating or electricity is available for preparing hot water.

The products of the invention can also be used as wrapping/packaging material which can be later on consumed.

The products are further available in all shapes, dimensions and formats, such as leaves, sticks, discs and the like, and can be customized with a logo.

In sum, the reconstituted plant products of the invention provide several benefits and advantages, such as
    the provision of products with higher extraction yield and extraction speed;
    the provision of a preferably dispersible and biodegradable product;

the ability to adjust the content of active ingredients (such as polyphenols, essential oils and the like) to provide a consistent composition;

the ability to adjust (reduce) the content of undesired constituents (such as pesticides, caffeine and the like);

the ability to provide new sensory characteristics (such as adjusting intensity of flavor, mixture of various plants and the like); and reduction of the bacterial load during the manufacturing process.

The following examples further describe and demonstrate embodiments that are within the scope of the present invention. The examples are given solely for the purpose of illustration, and are not to be construed as limitations of the present invention since many variations thereof are possible without departing from its spirit and scope.

EXAMPLES

Example 1

Method of Making the Reconstituted Plant Product

As raw material a black tea plant was used. The plant was mixed with water with a plant/water ratio of 1 to 5 by weight and the mixture was heated at 85° C. for 20 minutes, Subsequently, the aqueous portion was separated from the fibrous portion by an extraction step in a hydraulic press. Afterwards, the fibrous residue was again heated at 85° C. for 10 minutes with a plant/water ratio of 1 to 5 by weight. Again, the aqueous portion was separated from the fibrous portion by an extraction step in a hydraulic press. Then, the samples were refined in a Valley beater at 1.4% consistency for 10 minutes. As a next step, cellulosic fibers and in particular (a blend of abaca, hardwood and softwood pulps, with the respective ratios: 60/10/30) were added to the fibrous residue with a fibrous residue/woodpulp ratio of 5 to 1 in weight and hand sheets were made. The aqueous portion, which was separated by pressing, was concentrated in an evaporator to a solid concentration of 50%.

The concentrated aqueous portion was coated on the hand sheets on a manual size-press. The soluble level is typically between 27 and 37% in dry finished product. The soluble level of the reconstituted plant was approx. 27%, which is the soluble content of conventional plant used as the starting material of the experiment. The coated hand sheets were dried on a plate dryer. The obtained reconstituted plant product had the form of discs.

Comparison of Reconstituted Plant Product Versus Conventional Plant

The obtained reconstructed plant was tested for its properties. Also, a conventional black tea plant was packed into a conventional cellulosic bag for preparing a comparison infusion. For determining the properties the optical density of the solutions were measured at 274 nm. Both the reconstructed plant and the conventional plant were inserted into hot water (90° C.), Same weights of plant material and identical experimental conditions were used. A beaker was filled with 200 ml water (ref. Cristaline) and was heated at 90° C. At the starting point of the experiment, i.e. T=0, the heating was stopped and the bag with conventional black tea was immersed into water. To homogenize the content of the beaker during the entire experiment, a rotary magnet was used.

In steps of 30 seconds six samples of the water were taken. Then, the optical density of the sample was determined using a spectrophotometer at the wavelength of 274 nm. For the reference test a sample of clear water (Cristaline) heated at 90° C. was used. Then the same procedure was repeated with the bag comprising the reconstituted plant product according to the invention.

Figure 2:
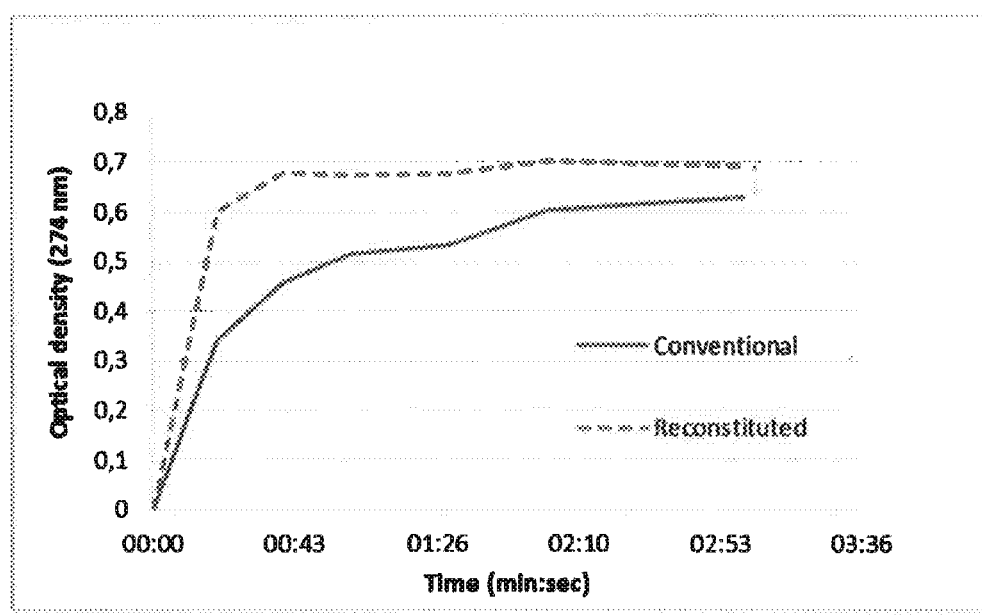
FIG. 2 is a graph showing total extraction time in hot water for an impregnated edible product as compared to a conventional plant in a bag.

As can be taken from FIG. 2, the optical density measured after 3 minutes of extraction for the reconstituted plant product was 0.69, whereas for the conventional plant 0.63 was measured. Hence, the product according to the invention provided a higher extraction rate of solubles as compared to a conventional plant product. In particular, the extraction ratio in this test was +10% as compared to the conventional bag. The reconstituted plant enabled a more efficient extraction (up to about 100% solubles were extracted from the plant). In other words, using the same amount of material, more solubles could be released from the reconstituted plant product according to the invention than from the conventional plant product in a standard cellulosic bag.

Similar results were obtained with different extraction times, or when the reconstituted plant was compared to natural black tea in loose form, i.e. without a cellulosic bag.

The above findings show the improved properties of the reconstructed plant. These findings, namely the improved substance release, are equally meaningful for other applications, e.g. with a different solvent or without a solvent.

Example 2

The reconstructed plant product obtained according to the method as explained in example 1 was used to determine a first extraction rate. On the other hand, natural black tea in a conventional cellulosic bag was used to determine a second extraction rate. The first and second extraction rates are representative of the speed soluble substances can be released from the plant products. The result is graphically shown in FIG. 3.

Figure 3:
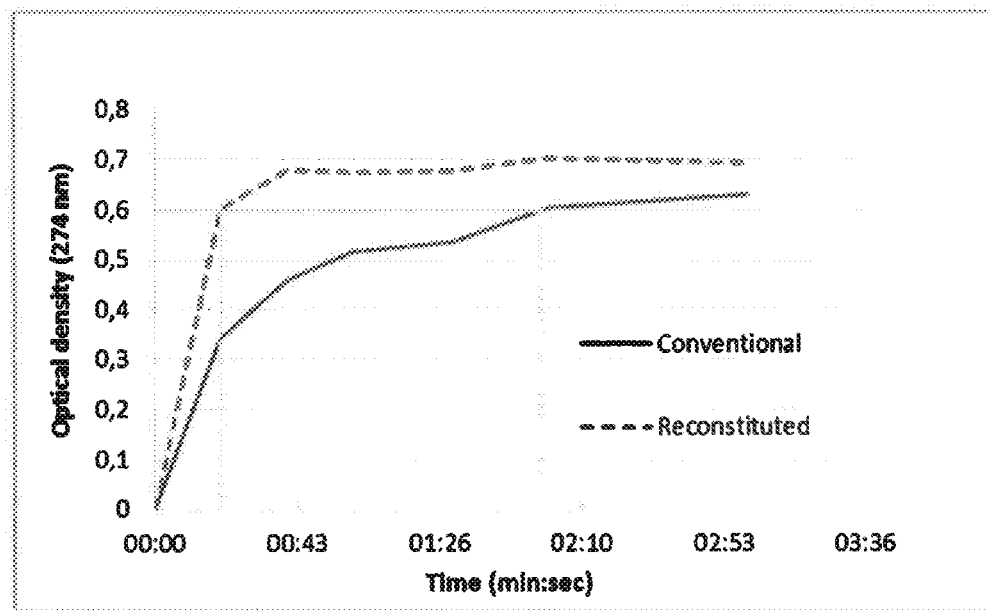
FIG. 3 is a graph showing total extraction time in hot water and the improved properties as regards the rate substances are released from the product according to the invention.

Like in example 1, the reconstituted plant was immersed into water at 90° C. and the optical density was measured over time. Likewise, the conventional plant product was immersed into water at 90° C. The more solubles are released from the plant, the higher the optical density of the respective water will be. As shown in FIG. 3, the optical density of the water with the reconstituted plant (dashed line) changes faster than the water with the conventional plant (continuous line). An optical density of 0.6 was reached by the reconstituted plant within 20 seconds. In contrast, the same optical density was reached by the conventional plant only after about 2 minutes.

This again shows that the reconstituted plant provides improved properties as regards the rate substances can be released from the plant product.

Similar results were obtained when reconstituted plant product was compared to natural black tea in loose form.

Example 3

In this example exactly the same setup was used as in example 2, only the water was at room temperature, i.e. 20° C.

Figure 4:
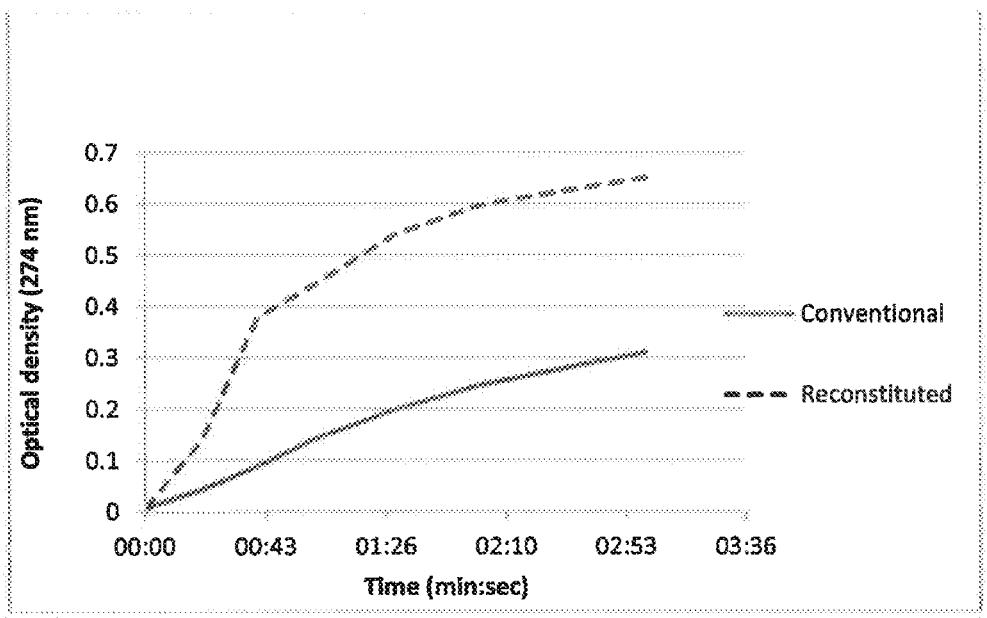
FIG. 4 is a graph showing total extraction time in cold water for an impregnated edible product as compared to a conventional plant in a bag.

As shown in FIG. 4, the optical density of the water with the reconstituted plant (dashed line) changes faster than the water with the conventional plant (continuous line). The water with the reconstituted plant reached an optical density of 0.3 within about 30 seconds and an optical density of 0.6 within about 2 minutes. In contrast, the conventional plant in a bag required about 6 times longer to provide the optical density of 0.3. Hence, the reconstituted plant product provides faster extraction than conventional plant in bags.

Similar results were obtained when reconstituted plant was compared to natural black tea in loose form.

Example 4

This example shall demonstrate the adjustability or lower than a standard) of the amount of solubles and active ingredients present on the reconstituted plant product. The soluble content was measured by determining the weight of a given sample before and after extraction.

Black tea was used to produce a reconstituted plant product according to the method of example 1. As control, a conventional black tea was used containing solubles in an amount of 26% (w/w).

By adjusting the coating ratio, the amount of solubles was adjusted in three different runs to 5% (w/w; decreased level), to 26% (w/w; standard level) and to 50% (w/w; increased level).

Due to the adjustability of the reconstituted product according to the invention it is possible to provide a consistent, standardized delivery level of soluble/active ingredients as compared to the natural products that generally show an inherent variability.

Example 5

In this example different reconstituted plant products were manufactured according to the method of example 1 and tested.
Sample 1 (Original Plant in Loose Form) For natural black tea in loose form the amount of solubles was determined to be around 30%.
Sample 2 (Original Plant in Cellulosic Bag)
For natural black tea, i.e. the same as in Sample 1, in a conventional double chamber cellulosic bag the amount of solubles was determined to be around 30%.
Sample 3 (Reconstituted Plant with Standard Amount of Solubles)
A reconstituted plant product according to the invention was made from black tea. The reconstituted plant product was in the form of disks and had a standard dry basis weight, i.e. 100 gsm. The amount of solubles, which corresponds to the coating ratio for the reconstituted sample, was the same as of the natural plant, i.e. 30%.
Sample 4 (Reconstituted Plant with Decreased Amount of Solubles)
A reconstituted plant product according to the invention was made from black tea. The reconstituted plant product was in the form of disks and had a standard dry basis weight. The amount of solubles was 20% and thus decreased in comparison with the standard of 30%.
Sample 5 (Reconstituted Plant with Increased Amount of Solubles)
A reconstituted plant product according to the invention was made from black tea. The reconstituted plant product was in the form of disks and had a standard dry basis weight. The amount of solubles was 50% and thus increased in comparison with the standard of 30%.
Sample 6 (Reconstituted Plant with Decreased Dry Basis Weight)
A reconstituted plant product according to the invention was made from black tea. The reconstituted plant product was in the form of disks and had a decreased dry basis weight of 60 gsm as compared to the standard dry basis weight of 100 gsm. The amount of solubles was the same as of the natural plant, i.e. 30%.

A comparison of the properties of the samples, in particular a comparison of sample 3 with samples 1 and 2; sample 3 with samples 4 and 5; and sample 3 with sample 6, confirmed the findings of the foregoing examples. That is, the reconstituted plant provides a better ratio of extraction and faster extraction and allows to adjust the amount of solubles/active ingredients released.

Example 6

Method of Making a Bag Comprising Reconstituted Plant Product

Black tea was mixed with water with a plant/water ratio of 1 to 5 by weight and the mixture was heated at 85° C. for 20 minutes. Subsequently, the aqueous portion was separated from the fibrous portion by an extraction step in a hydraulic press. Afterwards, the fibrous residue was again heated at 85° C. for 10 minutes with a plant/water ratio of 1 to 5 by weight. Again, the aqueous portion was separated from the fibrous portion by an extraction step in a hydraulic press. Then, the samples were refined in a Valley beater at 1.4% consistency for 10 minutes. As a next step, cellulosic fibers (a blend of abaca, hardwood and softwood pulps, with the respective ratios: 60/10/30) were added to the plant fibrous residue at various levels in order to prepare the different samples and make hand sheets. Hand sheets were later dried on a plate dryer.

The following ratios of plant/cellulosic fibers have been used for producing a bag;
first sample: 40/60 (w/w);
second sample 60/40 (w/third
sample 80/20 (w/w).
No plant extract was located on the bags but the sample bags were filled with conventional black tea.
Comparison of Bag Comprising Reconstituted Plant Product Versus Conventional Cellulosic Bag A bag produced according to the above method was compared to a conventional cellulosic bag containing the same amount of black tea.

Figure 5:
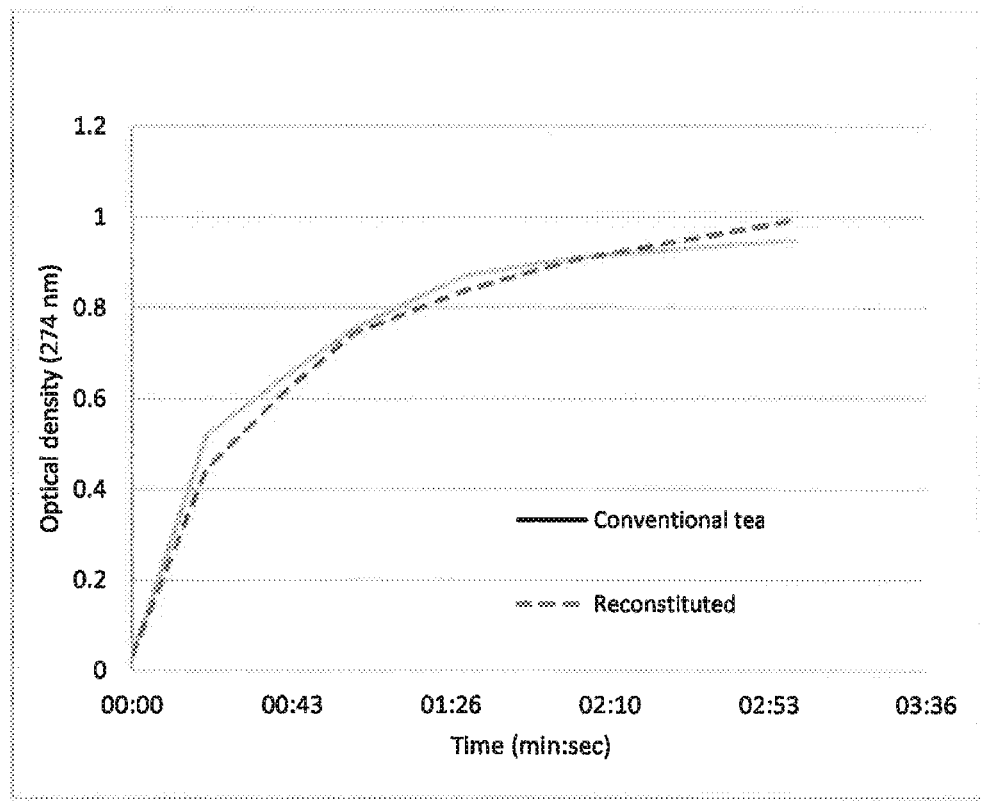
FIG. 5 is a graph showing extraction performance of a plant bag of the invention filled with conventional plant as compared to the extraction performance of a standard cellulosic plant bag filled with conventional plant.

The outcome was similar to examples 1 and 2. As can be taken from FIG. 5, the extraction performance of the sample corresponding to the 80/20 ratio (first sample) matched with the extraction performance of conventional cellulosic bags as measured by optical density.

Example 7

Plant extract from the extracting step was used to impregnate the fiber web of example 6 to obtain impregnated bags with an amount of plant extract from 5% to 50% of the total weight. The bags were filled with black tea.

The measurements of the extraction performance of the produced bags as compared to conventional cellulosic bags containing the same amount of plant revealed a similar outcome as examples 1 and 2. That is, from the bags according to the invention more solubles were released, and extraction rates were higher due to the additional release of substances from the coating (plant extract), in addition to natural extraction coming from the black tea which was contained in the bag.

One sample bag according to the invention was impregnated with plant extract as described above. Using water at 90° C., the product released 35% (w/w) plant solubles into the water.

Example 8

The following products were produced:
1) A product in the form of a plant bag was produced with about 5% solubles (w/w) and a dry basis weight of approx. 120 g/m² (w/w);
2) A product in the form of a plant bag was produced with about 5% solubles (w/w) and a dry basis weight of approx. 60 g/m² (w/w).

Both products were not filled with plant. Both bags have the same contact surface but have a different weight. The second plant bag having a dry basis weight of approx. 60 g/m² (w/w) is half the weight of the first plant bag having a dry basis weight of approx. 120 g/m² (w/w).

Figure 6:
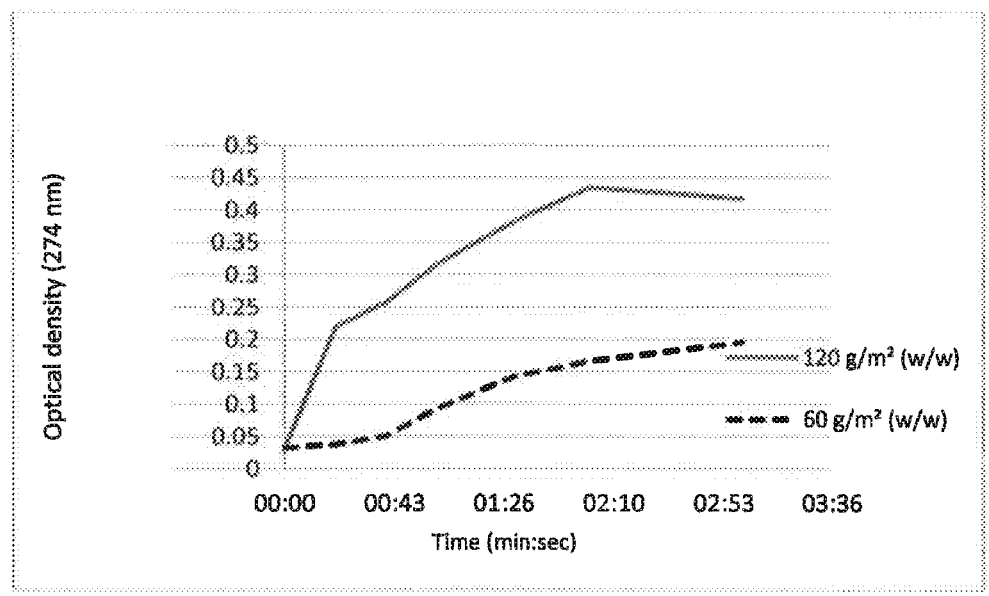
FIG. 6 is a graph showing extraction performance of a plant bag of the invention at a basis weight of 120 $g/m^2$ as compared to the extraction performance of a plant bag of the invention at a basis weight of 60 $g/m^2$.

As can be taken from FIG. 6, the first product comprising a dry basis weight of approx. 120 g/m² (w/w) releases more substances in shorter time as the second product comprising a lower dry basis weight of approx. 60 g/m² (w/w). In other words, release of solubles can be driven by the basis weight of the finished product.

Example 9

Example 1 described above was repeated with the additional use of a wet strength agent (here: cationic polyamide amine resin), in order to reduce potential degradation of some of the reconstituted material in water. The wet strength agent was added to the fibrous portion.

A tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. The soluble level is typically between 27 and 37% in dry finished product. In this example, soluble level of the reconstituted tea was approx. 27%, which is the soluble content of conventional tea used as the starting material of the experiment. The coated hand sheets were dried on a plate dryer. Infusion trials were run in hot water (approx. 90° C.) and product with wet strength agent showed less degradability into water than same material without agent.

Figure 7:
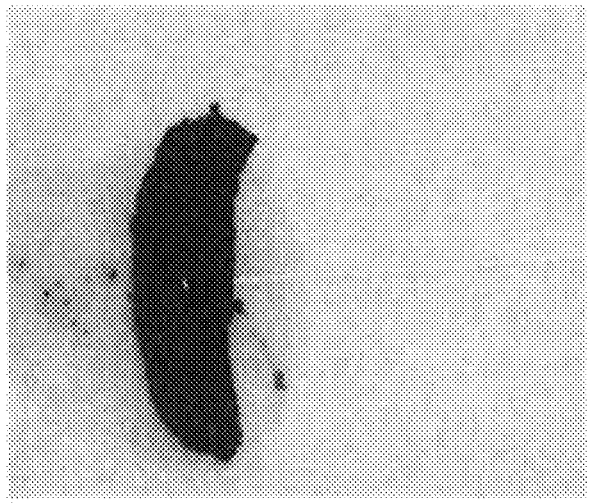
FIG. 7 shows reconstituted tea in one example without the use of a wet strength agent after 3 mins of infusion. The photograph shows that material is degraded.

FIG. 7 shows reconstituted tea in one example without the use of a wet strength agent after 3 mins of infusion. The photograph shows that material is degraded.

Figure 8:
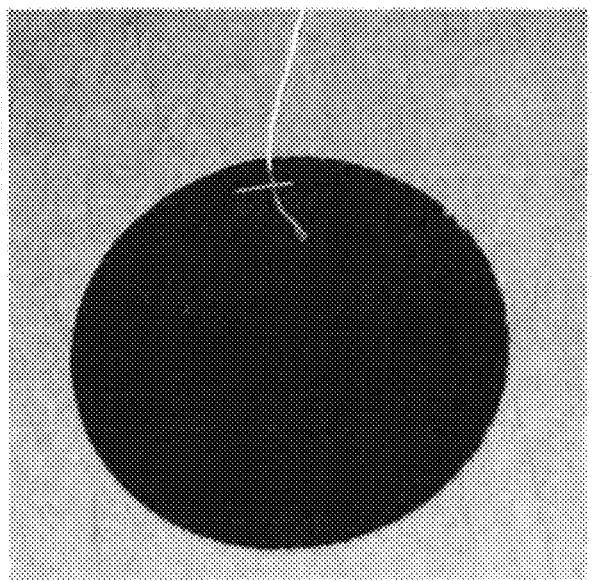
FIG. 8 shows reconstituted tea in this example with the use of a wet strength agent after 3 mins of infusion. The photograph shows that the material is substantially undegraded.

FIG. 8 shows reconstituted tea in this example with the use of a wet strength agent after 3 mins of infusion. The photograph shows that the material is substantially undegraded.

Example 10

In order to determine the effect of reconstituted plant soluble content and the dry basis weights on the infusion profile, a tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. The soluble level is typically between 27 and 37% in dry finished product. In this example, the following products were prepared:

Product A: soluble level of the reconstituted tea was 22%, which is the soluble content of conventional tea used as the starting material of the experiment. Dry basis weight of the material was 70 grs per m² (dry basis);

Product C: soluble level of the reconstituted tea was 22%, which is the soluble content of conventional tea used as the starting material of the experiment. Dry basis weight of this material was 170 grs per m² (dry basis) which is 143% higher than A; Product D: soluble level of the reconstituted tea was 38% which is 73% higher than A. Dry basis weight of D material was 170 grs per m² (dry basis).

The coated hand sheets were dried on a plate dryer.

The products (A, C and D) obtained in this example were tested for their properties including sensory properties, their propensity to release plant extract by preparing tea and compared. Both products were used to make tea, and the optical density of the solution (tea) was measured at 274 nm. For all samples, the total infusion time in hot water (90° C.) was 5 minutes. Same weights of tea material (2, 5 grs) and identical experimental conditions were used: a beaker containing 500 ml water was heated at 90° C. At T=0, i.e. upon start of the experiment, heating was stopped and a tea strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 274 nm (maximum absorption of caffeine). The reference/blank test was run with a sample of clear water heated at 90° C.

Figure 9:
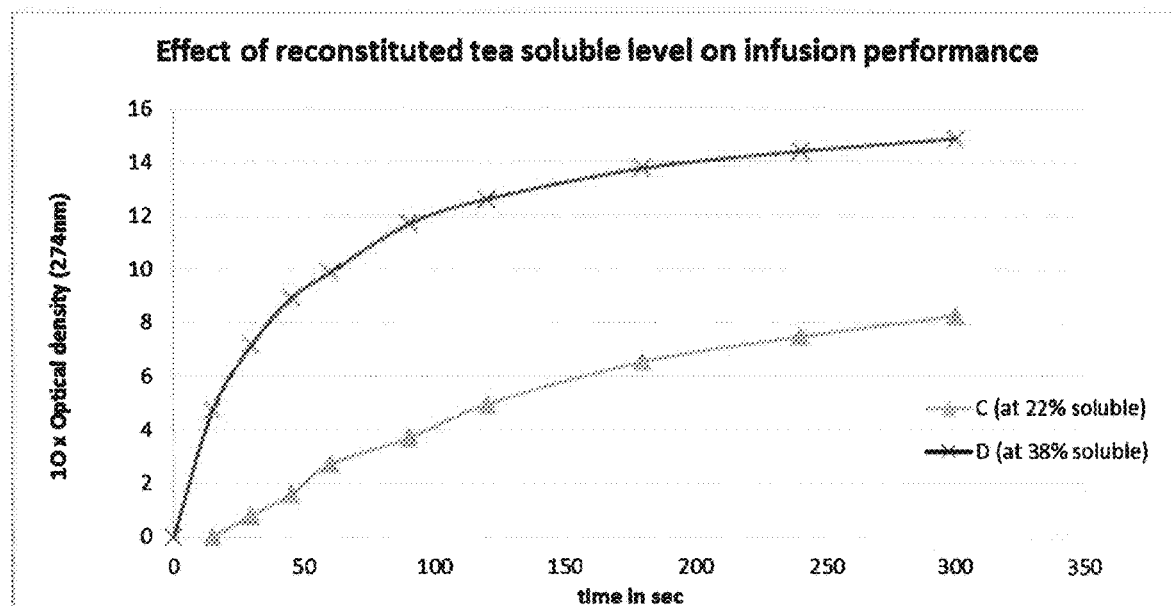
FIG. 9 shows a reconstituted material produced according to Example 10. Reconstituted tea (D—high soluble content) shows a higher infusion level of tea solubles than C (standard soluble level).
Figure 10:
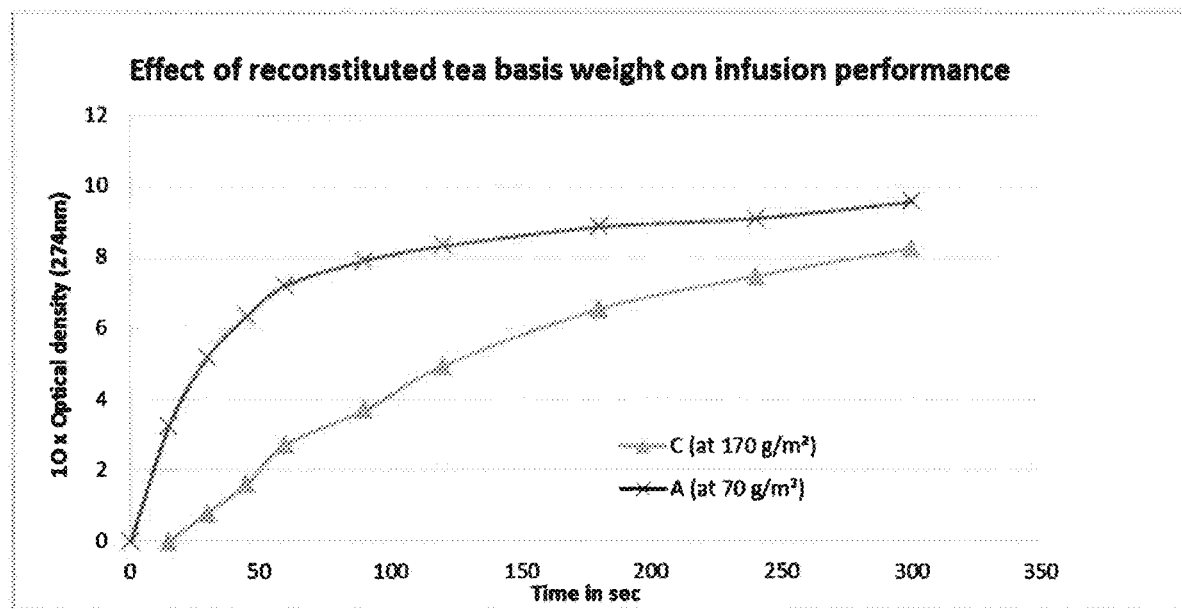
FIG. 10 shows a reconstituted material produced according to Example 10. Reconstituted tea A with a lower basis weight shows a faster infusion level of tea solubles than C.

The result is graphically shown in FIGS. 9 and 10.

FIG. 9: Reconstituted tea (D—high soluble content) shows a higher infusion level of tea solubles than C (standard soluble level). In order to reach an infusion level of 8.3 (expressed by 10×optical density at 274 nm), it takes 300 sec with sample C whereas only 40 sec are needed for D material (87% faster). Sensory evaluation performed by panel group also showed a stronger tea flavor and taste with D than with C. This demonstrates that product taste can be adjusted thanks to soluble content of reconstituted tea material.

FIG. 10 shows that reconstituted tea A with a lower basis weight shows a faster infusion level of tea solubles than C. Figures show that infusion rate of 8, 3 (expressed by 10×optical density at 274 nm) is reached in 120 sec for A sample whereas 300 sec are needed for C. Infusion with A is 60% faster than with C. Actually, a lower basis weight for a given weight of material entails a more important contact surface which, at the end, improves infusion kinetics.

Example 11

In order to determine the effect of the reconstitution process on the green tea product sensory profile, a tea product was made according to the following method: a green tea (Sencha from China) was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 36% extract content, which is the soluble content of the starting material of the experiment. The coated hand sheets were dried on a plate dryer.

Figure 11:
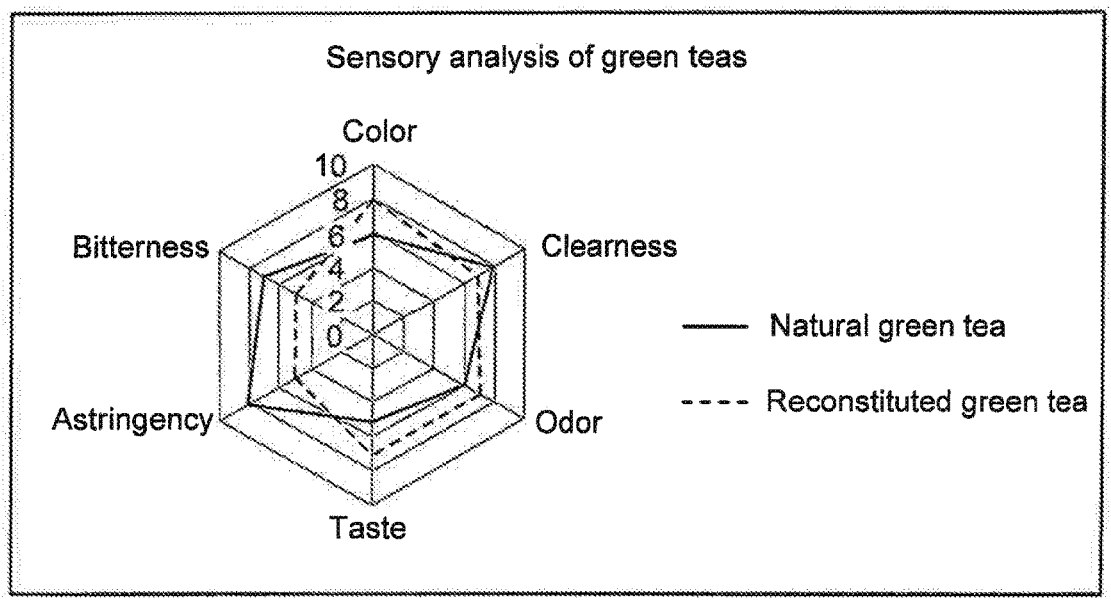
FIG. 11 shows the sensorial profile of reconstituted green tea and natural material.

The product obtained in this example was tested for its sensory properties and compared to natural tea material used for the experiment as described above. Both products were used to make tea. For all samples, the total infusion time in hot water (90° C.) was 5 minutes. Same weights of tea material (2 grs) and identical experimental conditions were used: a beaker containing 200 ml water was heated at 90° C. and tea materials were immersed into water. Then, after 5 minutes, sensory profile of both products was performed. The result is graphically shown in FIG. 11.

The experiment shows that the odor, color and taste are higher in the reconstituted tea than in the natural material. However, astringency and bitterness are significantly lower in the reconstituted tea than natural material.

Example 12

Reconstitution of Rooibos Leaves

A reconstituted product was made according to the following method: Rooibos (*Aspalathus linearis*) was initially heated at 85° C. for 20 minutes with a rooibos/water ratio of 1 to 5 by weight. This was followed by an extraction step in a hydraulic press to separate the aqueous portion from the rooibos fiber portion. The recovered rooibos fiber portion was again heated at 85° C. for 10 minutes with a rooibos/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the rooibos fibrous residue with a rooibos fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 22% extract content, which is the soluble content of the starting material of the experiment. The coated hand sheets were dried on a plate dryer.

Figure 12:
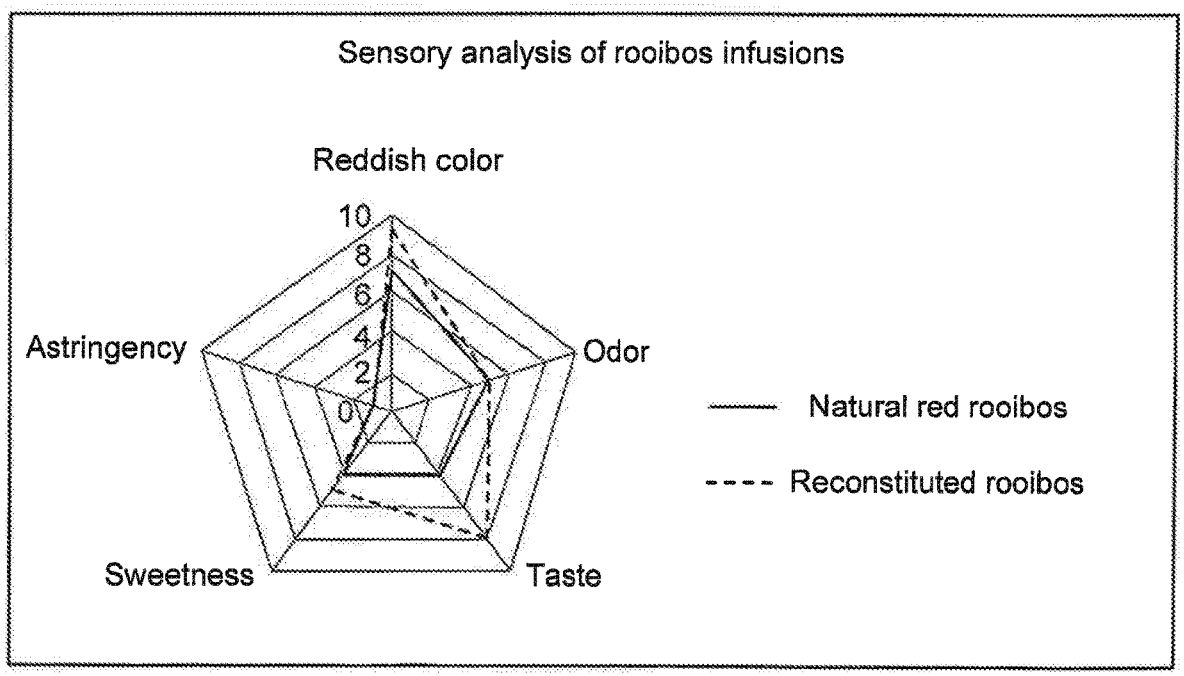
FIG. 12 shows the sensory analysis of reconstituted rooibos and natural material (rooibos leaves).

The product obtained in this example was tested for its sensory properties and compared to natural rooibos material used for the experiment as described above. Both products were used to make a rooibos beverage. For all samples, the total infusion time in hot water (90° C.) was 5 minutes. Same weights of rooibos material (2 grs) and identical experimental conditions were used: a beaker containing 200 ml water was heated at 90° C. and rooibos materials were immersed into water. Then, after 5 minutes, sensory profile of both products was performed. The result is graphically shown in FIG. 12.

The experiment demonstrates that reconstituted rooibos tea shows a stronger taste than original material. Moreover, color is stronger.

The reconstituted rooibos obtained in this example and its original material were tested for their properties in preparing infusion and compared. Both products were used to make infusion, and the optical density of the solution was measured at 450 nm. For all samples, the total infusion time in hot water (90° C.) was 5 minutes. Same weights of materials (2, 5 grs) and identical experimental conditions were used: a beaker containing 500 ml water was heated at 90° C. At T=0, i.e. upon start of the experiment, heating was stopped and a reconstituted rooibos strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 450 nm (maximum absorption of lutein). The reference/blank test was run with a sample of clear water heated at 90° C.

Figure 13:
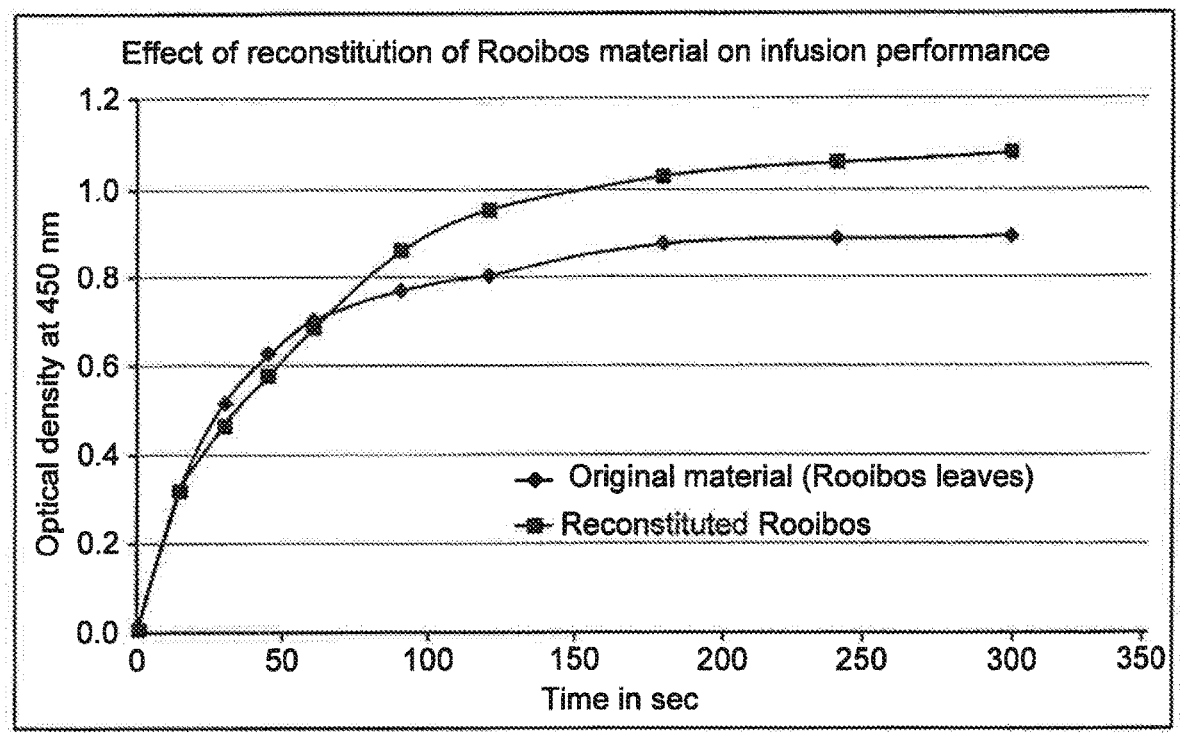
FIG. 13 shows the infusion performance of a reconstituted Rooibos material.

The infusion performance for reconstituted Rooibos material is graphically shown in FIG. 13. Infusions of rooibos products are comparable. However, it is demonstrated that reconstituted rooibos offers a more complete extraction. After 5 mins infusion, optical density of liquor made of reconstituted rooibos is 1.1 compared 0.9 for original material (+22%).

Example 13

Reconstitution of Thyme Leaves

Figure 14:
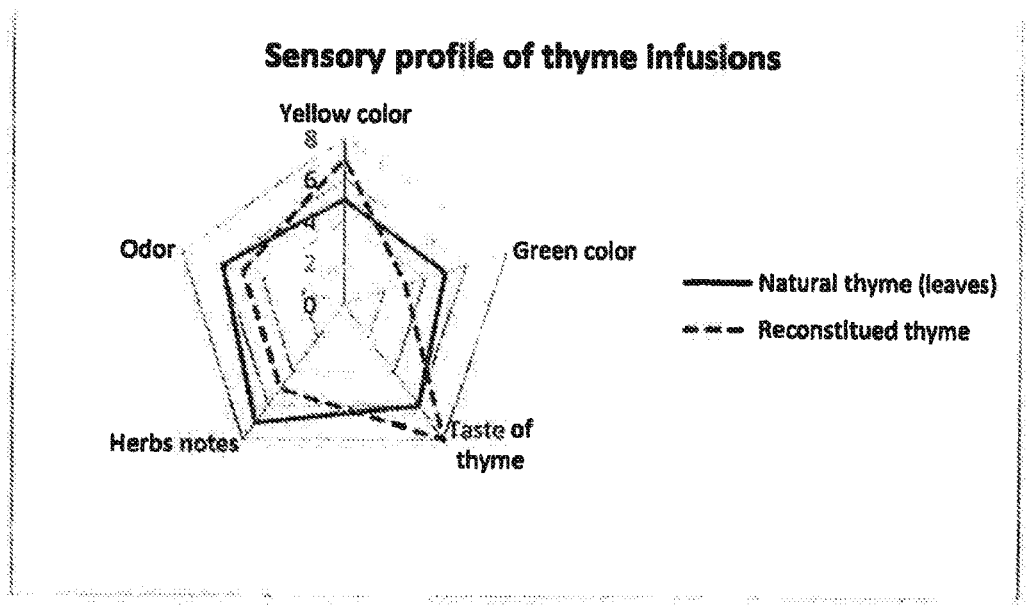
FIG. 14 shows the sensory profile of thyme leaves as compared to reconstituted thyme.

A reconstituted product was made according to the following method: Thyme (*Thymus vulgaris*) was initially heated at 85° C. for 20 minutes with a thyme/water ratio of 1 to 5 by weight. This was followed by an extraction step in a hydraulic press to separate the aqueous portion from the thyme fiber portion. The recovered thyme fiber portion was again heated at 85° C. for 10 minutes with a thyme/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the thyme fibrous residue with a thyme fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 30% extract content, which is the soluble content of the starting material of the experiment. The coated hand sheets were dried on a plate dryer. The product obtained in this example was tested for its sensory properties and compared to natural thyme material used for the experiment as described above. Both products were used to make a thyme beverage. For all samples, the total infusion time in hot water (90° C.) was 5 minutes. Same weights of thyme material (2 grs) and identical experimental conditions were used: a beaker containing 200 ml water was heated at 90° C. and thyme materials were immersed into water. Then, after 5 minutes, sensory profile of both products was performed. The result is graphically shown in FIG. 14.

The experiment shows that that the color is rather yellow for the reconstituted thyme and rather green for the natural leaves. Global odor and herbal notes are higher for the natural thyme. However, the taste of thyme is higher in the reconstituted material.

The reconstituted thyme obtained in this example and its original material were tested for their properties in preparing infusion and compared. Both products were used to make infusion, and the optical density of the solution was measured at 326 nm. For all samples, the total infusion time in hot water (90° C.) was 5 minutes. Same weights of materials (2, 5 grs) and identical experimental conditions were used: a beaker containing 500 ml water was heated at 90° C. At T=0, i.e. upon start of the experiment, heating was stopped and a reconstituted thyme strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 326 nm (maximum absorption of rosmarinic acid). The reference/blank test was run with a sample of clear water heated at 90° C. The result is shown in FIG. 15.

Figure 15:
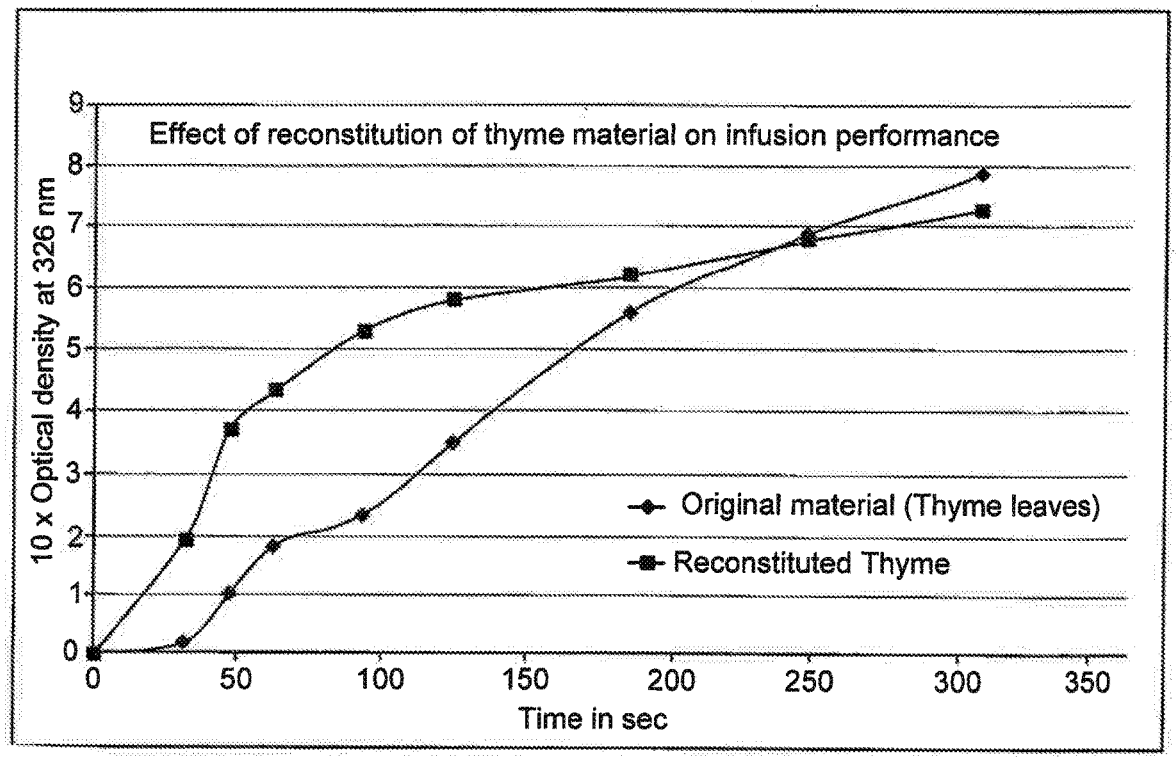
FIG. 15 shows the infusion performance of a reconstituted thyme material.

FIG. 15 shows that reconstituted thyme infusion occurs very quickly. After 90 sec infusion, optical density of original material is 2.3 whereas liquor from reconstituted thyme optical density is 5.3 which is 130% higher.

Reconstitution of Thyme and Black Tea Leaves

A reconstituted product was made according to the following method: Thyme (*Thymus vulgaris*) and black tea (*Camelia sinensis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a blend/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/wood pulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 25% extract content, which is the balanced soluble content of the materials of the experiment. The coated hand sheets were dried on a plate dryer.

Figure 16:
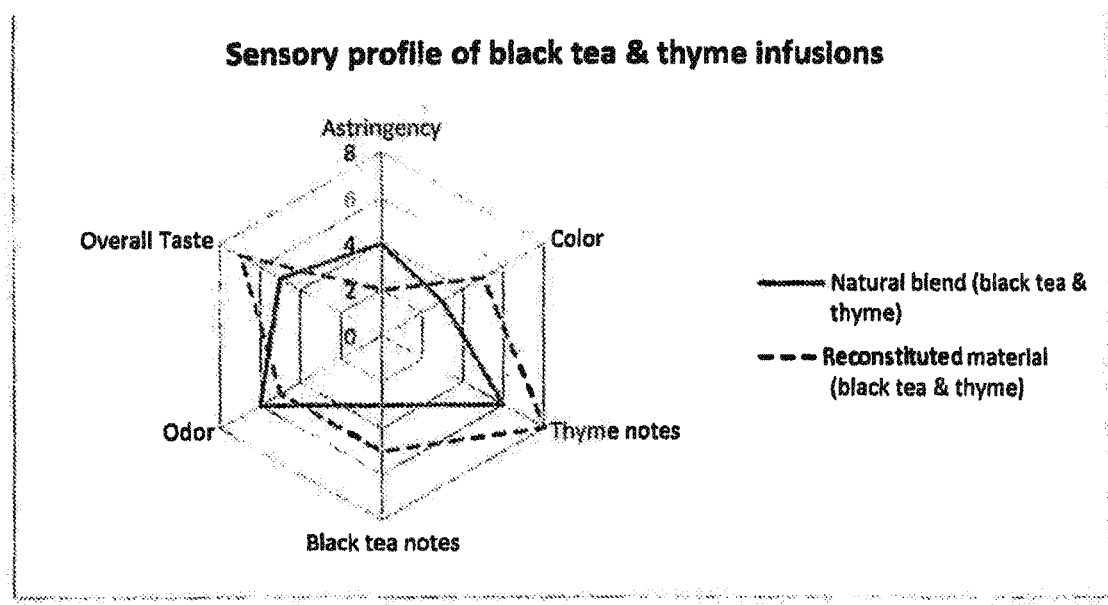
FIG. 16 shows the sensory analysis of reconstituted thyme black tea as compared to the natural blend.

The product obtained in this example was tested for its sensory properties and compared to natural blend material used for the experiment as described above. Both products were used to make the infusion. For all samples, the total infusion time in hot water (90° C.) was 5 minutes. Same weights of material (2 grs) and identical experimental conditions were used: a beaker containing 200 ml water was heated at 90° C. and blend was immersed into water. Then, after 5 minutes, sensory profile of both products was performed. The result is graphically shown in FIG. 16.

The experiment shows that color and overall taste are higher in the reconstituted leaves. Also, thyme and black tea notes are higher. But the astringency of the product is lower in the reconstituted material.

Example 15

Reconstitution of Thyme and Laurel Leaves ("*Bouquet garni*")

A reconstituted product was made according to the following method: Thyme (*Thymus vulgaris*) and Laurel (*Laurus nobilis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/woodpulp ratio of 5 to 1 in weight and a wet strength agent was then added to the fibrous portion at a level of 5% why in order to make hand sheets. The aqueous portion was concentrated in an evaporator to a solid concentration of 50% and then coated on a hand sheet on a manual size-press. In this example, the product was produced at 34% extract content which is the balanced soluble content of the materials of the experiment. The coated hand sheets were dried on a plate dryer.

Figure 17:
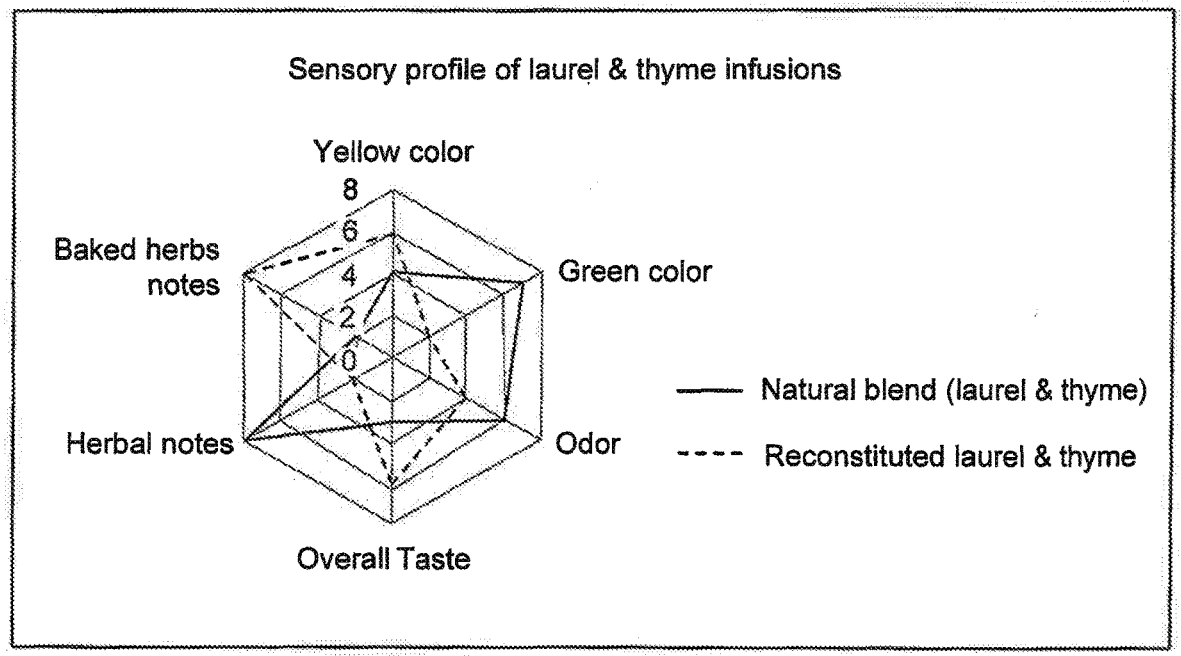
FIG. 17 shows the sensory analysis of reconstituted laurel & thyme vs natural blend (laurel & thyme leaves).

The product obtained in this example was tested for its sensory properties and compared to natural tea material used for the experiment as described above. Both products were used to make tea. For all samples, the total infusion time in hot water (90° C.) was 5 minutes, Same weights of tea material (2 grs) and identical experimental conditions were used: a beaker containing 200 ml water was heated at 90° C. and tea materials were immersed into water. Then, after 5 minutes, sensory profile of both products was performed. The result is graphically shown in FIG. 17.

The experiment shows that the two products are very different. The color is rather yellow for reconstituted product and green for the original blend. The taste is on the herbal side for the original blend and more on the baked side for the reconstituted material. Globally, taste and odor are higher for the original blend. Taste and odor can, however be adjusted and increased for the reconstituted material by increasing soluble content of reconstituted material or by adding ingredients such as food flavors, food dyes or other plant extracts having color and aroma properties.

Figure 22:
FIG. 22 shows a photograph of a reconstituted sheet of product placed on a meat and rolled.

Also, same reconstituted product was used for cooking purposes. A sheet of product was put onto the surface of chicken breast and rolled so to place the product in the middle of the meat as illustrated in FIG. 22. Chicken was then cooked. Evaluation showed a distinctive and pleasant taste of herbs.

Example 16

Reconstitution of Mint Leaves

A reconstituted product was made according to the following method: Mint (*Mentha* x *piperita*) was initially heated at 85° C. for 20 minutes with a mint/water ratio of 1 to 5 by weight. This was followed by an extraction step in a hydraulic press to separate the aqueous portion from the rooibos fiber portion. The recovered mint fiber portion was again heated at 85° C. for 10 minutes with a mint/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the mint fibrous residue with a mint fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 50% extract content, which is the soluble content of the starting material of the experiment. The coated hand sheets were dried on a plate dryer.

Figure 18:
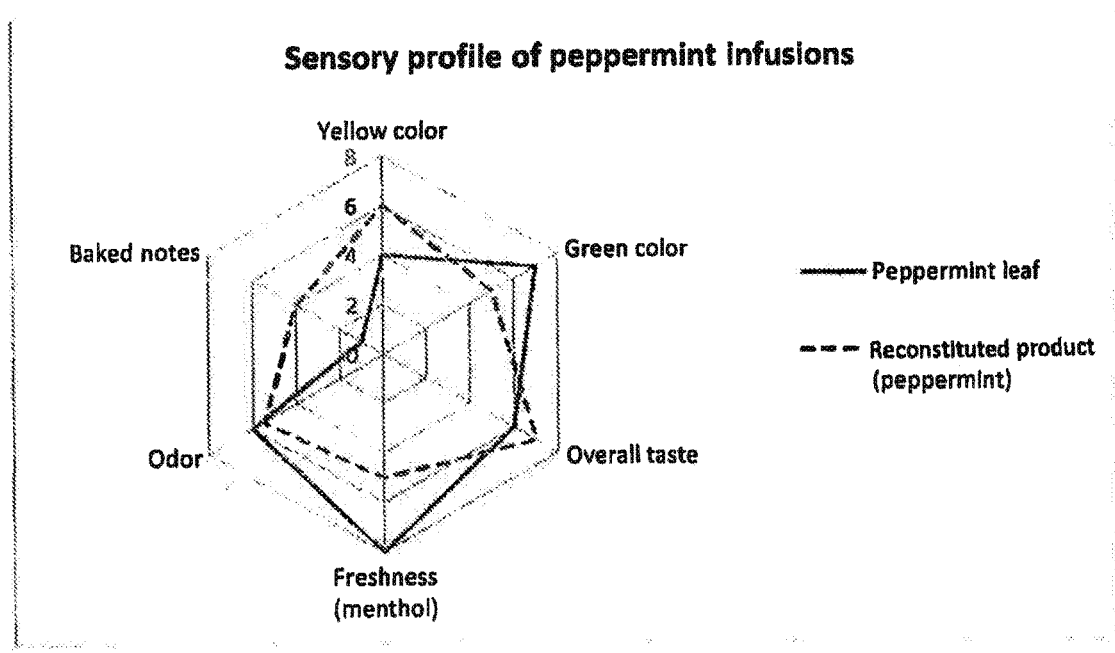
FIG. 18 shows the sensory analysis of reconstituted mint vs original mint material (*Mentha* x *piperita*).

The product obtained in this example was tested for its sensory properties and compared to natural mint material used for the experiment as described above. Both products were used to make a mint beverage. For all samples, the total infusion time in hot water (90° C.) was 5 minutes. Same weights of mint material (2 grs) and identical experimental conditions were used: a beaker containing 200 ml water was heated at 90° C. and mint material was immersed into water. Then, after 5 minutes, sensory profile of both products was performed. The result is graphically shown in FIG. 18.

The experiment shows that in the reconstituted product, freshness/menthol notes have been reduced vs original mint material; however, overall taste is stronger.

Example 17

Reconstitution of Mint (*Mentha* x *piperita*) and Green Tea Leaves (*Camellia sinensis*)

A reconstituted product was made according to the following method: Mint (*Mentha* x *piperita*) and Green Tea leaves (*Camellia sinensis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a blend/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/wood pulp ratio of 5 to 1 in weight in order to make hand sheets. The aqueous portion was concentrated in an evaporator to a solid concentration of 50% and L-menthol was added to the solution at 6% and then coated on a hand sheet on a manual size-press. In this example, the product was produced at 35% extract content, which is the balanced soluble content of the materials of the experiment. The coated hand sheets were dried on a plate dryer.

Figure 19:
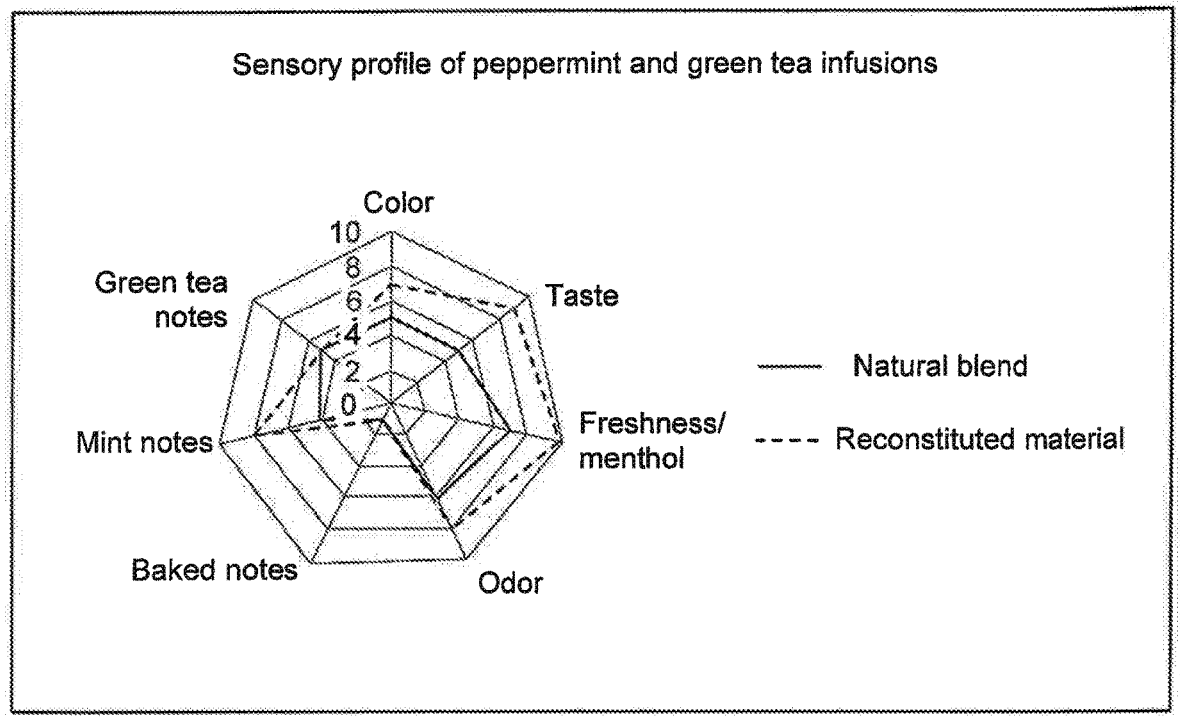
FIG. 19 shows the sensory analysis of reconstituted mint and green ea vs original blend.
Figure 20A:
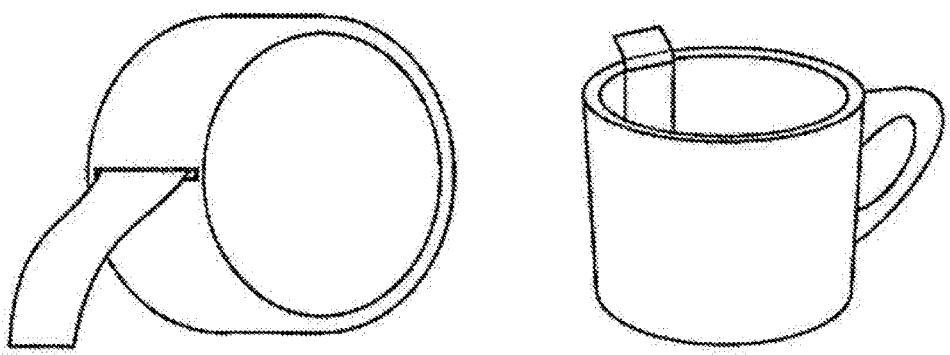
FIG. 20A-K shows reconstituted material in different physical shapes that provide for different kinds of applications.
Figure 20B:
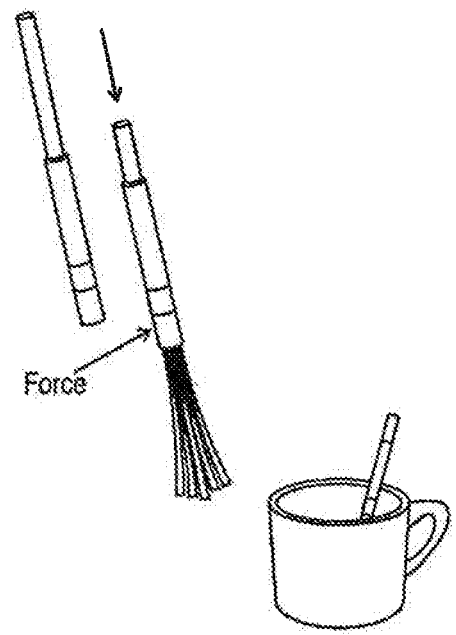
Figure 20C:
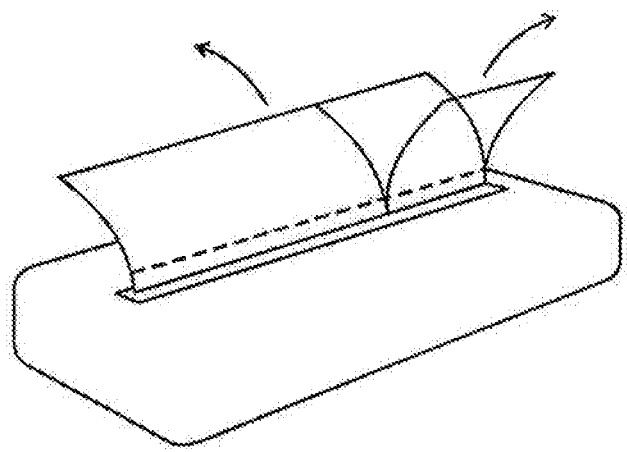
Figure 20C:
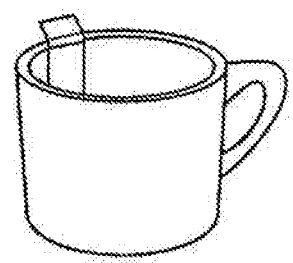
Figure 20D:
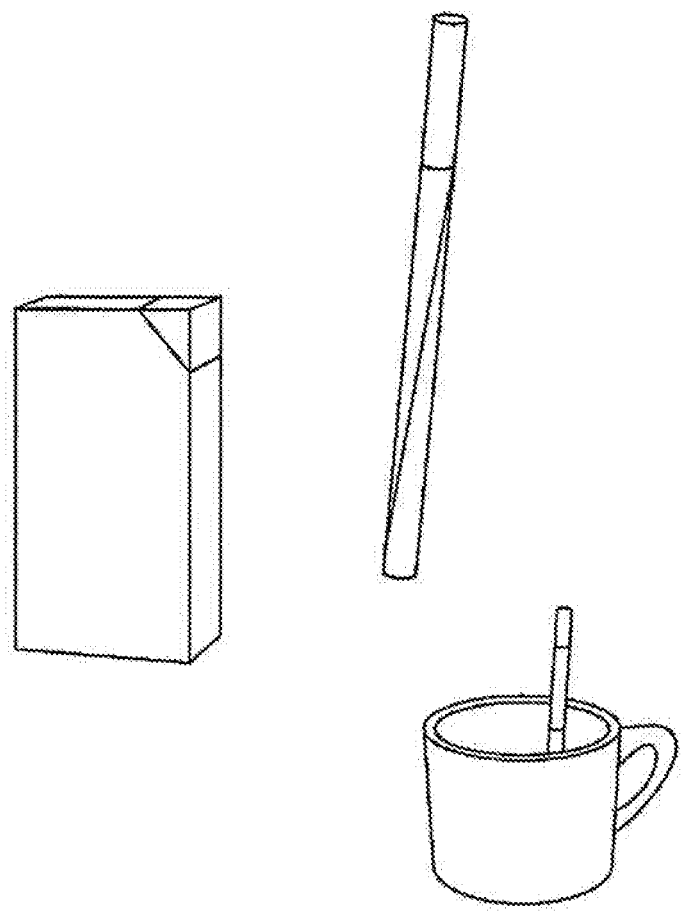
Figure 20E:
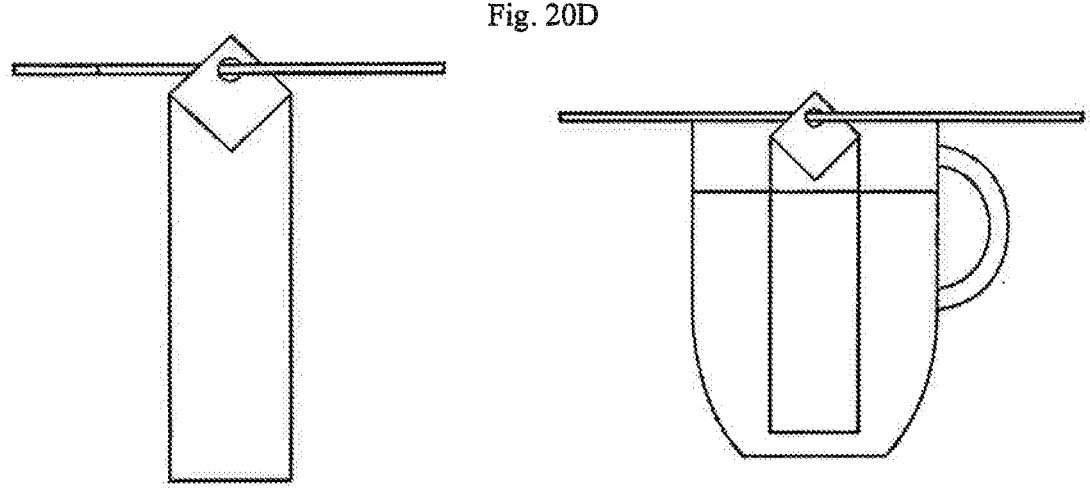
Figure 20F:
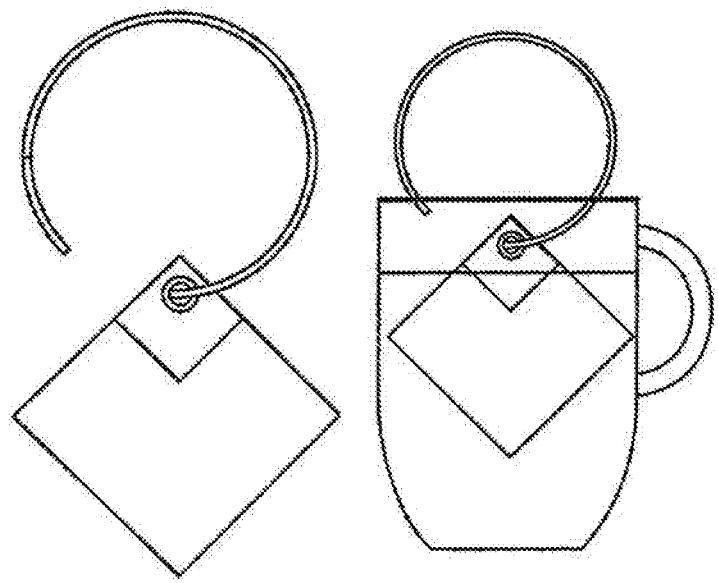
Figure 20G:
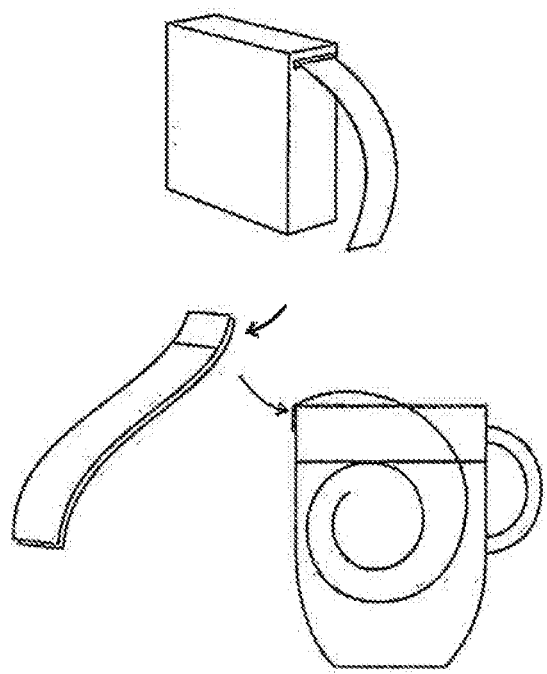
Figure 20H:
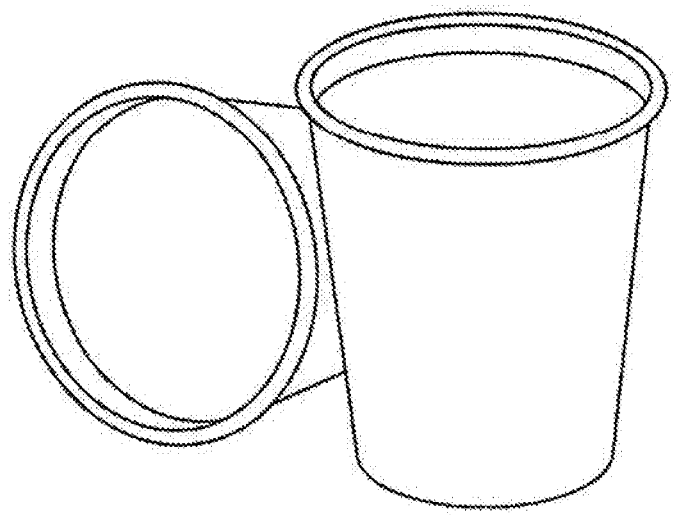
Figure 20I:
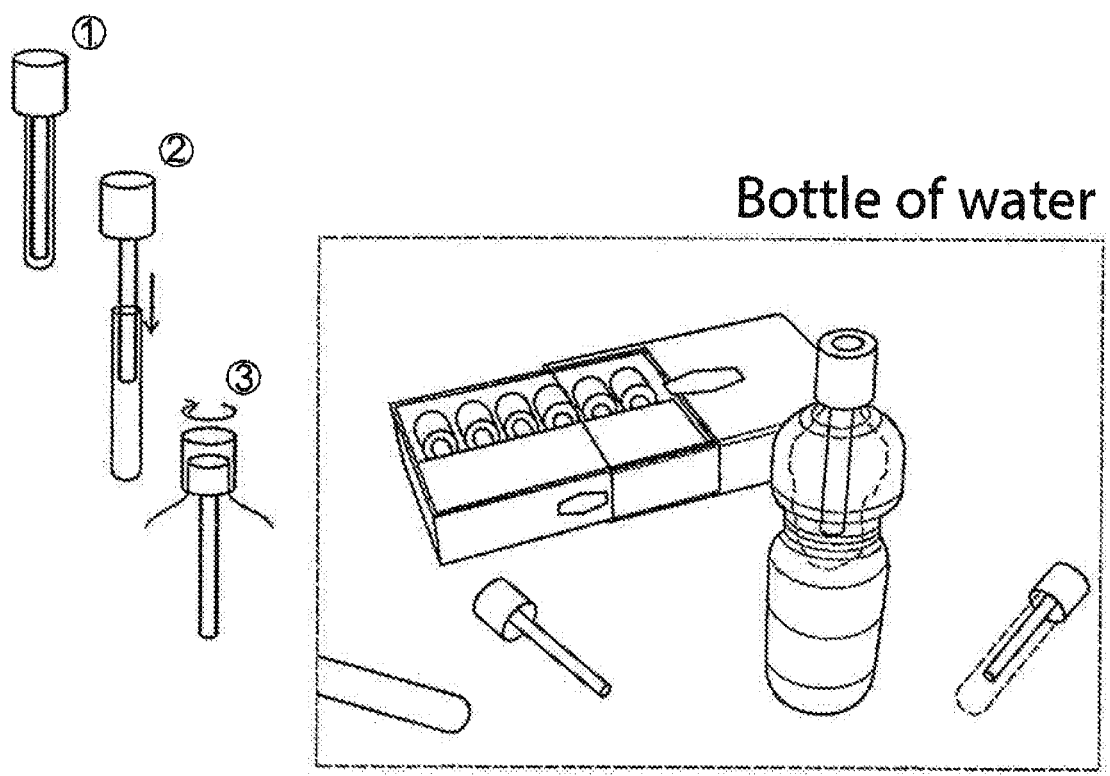
Figure 20J:
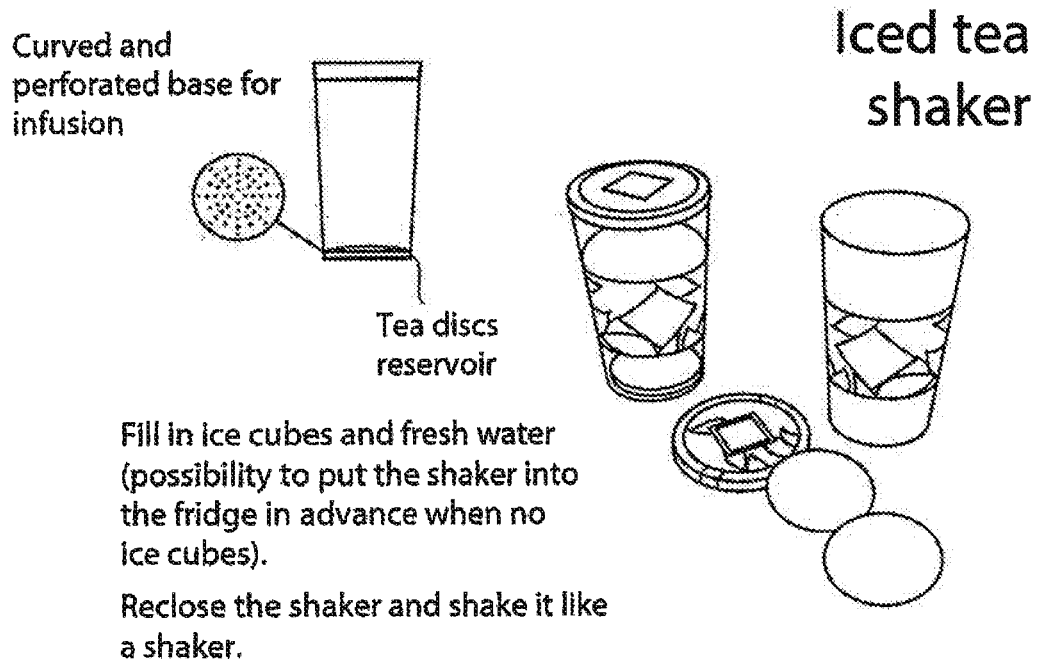
Figure 20K:
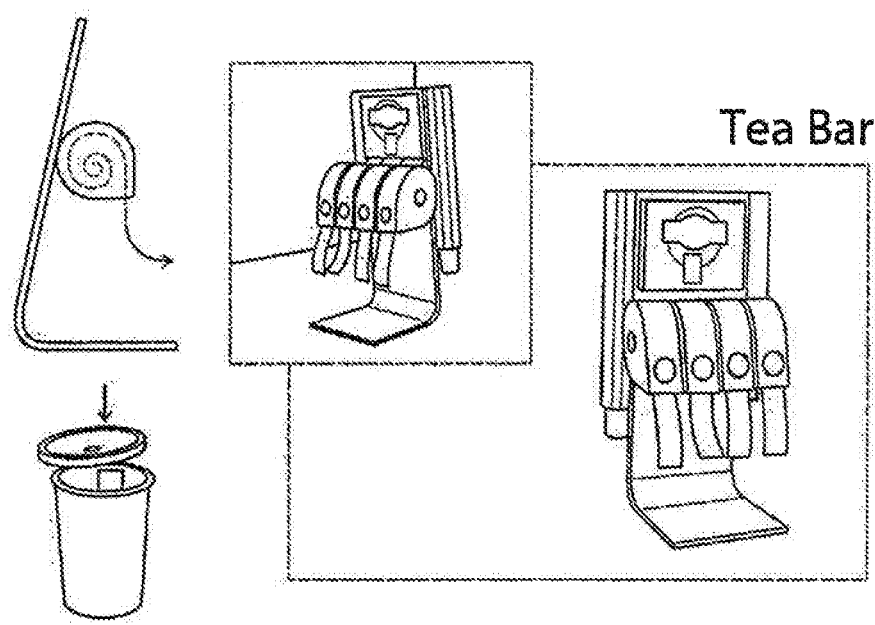

The product obtained in this example was tested for its sensory properties and compared to natural blend material used for the experiment as described above. Both products were used to make the infusion. For all samples, the total infusion time in hot water (90° C.) was 5 minutes. Same weights of material (2 grs) and identical experimental conditions were used: a beaker containing 200 ml water was heated at 90° C. and blend was immersed into water. Then, after 5 minutes, sensory profile of both products was performed. The result is graphically shown in FIG. 19.

Example 18

Removal of Caffeine from Tea Leaves Thanks to the Reconstitution Process

In order to illustrate the potential of the invention to reduce the amount of specific components from tea, a treatment to decrease caffeine content from tea was developed and tested at the lab scale.

Literature shows that alkaloids compounds such as caffeine are extracted in the soluble portion. Therefore, experiment has been run on the liquor part of tea, after separation step.

A black tea was initially heated at 85° C. for 20 minutes with a tea/water ratio of 1 to 5 by weight. This was followed by an extraction step in a hydraulic press to separate the aqueous portion from the tea fiber portion. The aqueous portion of tea was then mixed with activated charcoal in powder form. Approx. 23 g of activated charcoal was added to 500 ml of tea liquor and mixed at 60° C., stirred at 350 rpm for 1 hour. After filtration, caffeine levels in liquors were measured then through LC-MS method.

The following samples were produced:
Control: standard tea liquor without activated charcoal treatment
A: Tea liquor treated with activated charcoal Acticarbone P13 from CECA
B: Tea liquor treated with activated charcoal Acticarbone 2SW from CECA
C Tea liquor treated with activated charcoal Acticarbone 3SA from CECA
D Tea liquor treated with activated charcoal Acticarbone CPL from CECA
Caffeine contents in tea liquors are as follows:
Control: 22700 mg/Kg
A: <10 mg/Kg
B: <10 mg/Kg
C: <10 mg/Kg
D: <14 mg/Kg
It can be seen that caffeine levels are strongly reduced by using activated charcoal on tea liquor.

Example 19

Reduction of Microbiological Load of Tea Through the Reconstituted Process

Reconstituted tea material produced during experiment 7 was analyzed vs original tea material. Bacteria counts were run (Aerobic Plate Count after 48 hrs at 30° C.). Results are shown in the following table:

|  | Total Aerobic bacteria count (units/grs) |
| --- | --- |
| Original tea material | $8.3 \; 10^4$ |
| Reconstituted teas | $1.4 \; 10^3$ |

Results show that reconstitution process does reduce the microbiological load. Temperatures applied all along the process have a lethal effect of microorganisms.

Example 20

Reconstituted material was produced in different physical shapes that provide for different kinds of applications.

Specifically, the products shown in FIG. 20 are examples that allow for convenient preparation of tea infusions.

Example 21

A reconstituted product was made according to the following method: coffee (*Coffea* spp) was initially heated at 60° C. for 20 minutes with a coffee/water ratio of 1 to 5 by weight. This was followed by an extraction step in a hydraulic press to separate the aqueous portion from the coffee fiber portion. The recovered coffee fiber portion was again heated at 60° C. for 10 minutes with a coffee/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios 60/10/30) were added to the coffee fibrous residue with a coffee fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 30% extract content, which is the soluble content of the starting material of the experiment. The coated hand sheets were dried on a plate dryer.

The product obtained in this example was tested for its properties in preparing coffee and compared to original material. Both products were used to make coffee, and the optical density of the solution (coffee) was measured at 274 nm. For all samples, the total infusion time in hot water (90° C.) was 5 minutes. Same weights of coffee material (2, 5 grs) and identical experimental conditions were used: a beaker containing 500 ml water was heated at 90° C. At T=0 i.e. upon start of the experiment, heating was stopped and a coffee strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 274 nm (maximum absorption of caffeine). The reference/blank test was run with a sample of clear water heated at 90° C.

Figure 21:
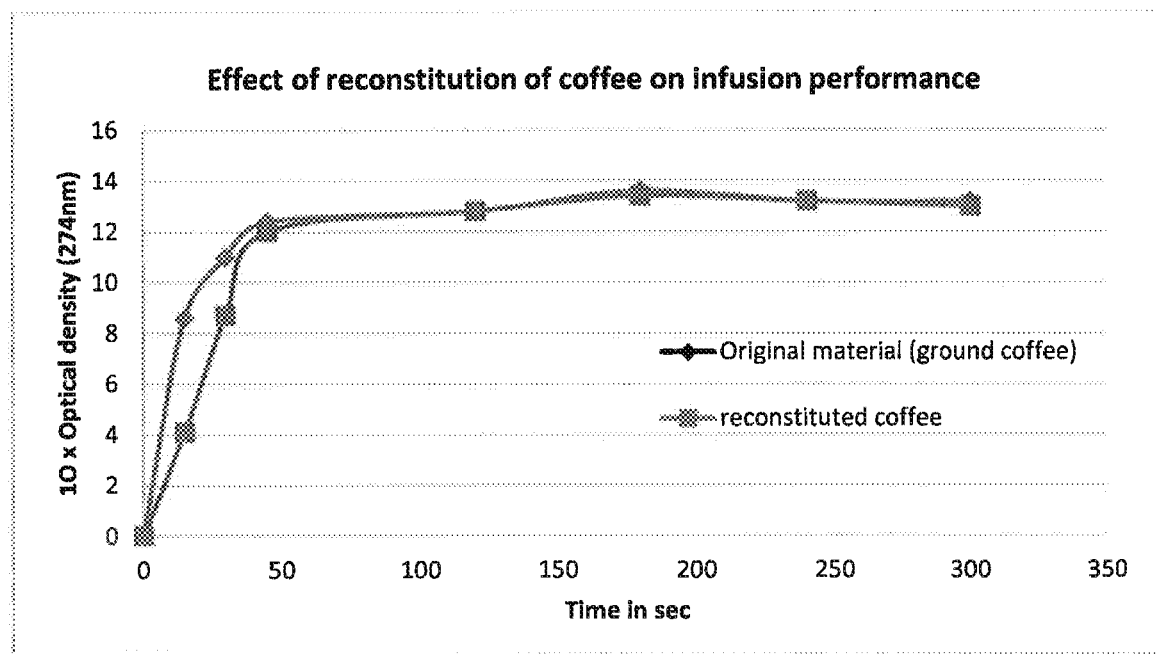
FIG. 21 shows the infusion performance of a reconstituted coffee material.

The result is graphically shown in FIG. 21 below.

While infusion prepared with original coffee material is faster during the first 50 seconds, after 1 minute, infusion profiles of both samples are similar.

Example 22

Reconstitution of Cocoa Shells

A reconstituted product was made according to the following method: cocoa shells (*Theobroma cacao*) were initially heated at 60° C. for 20 minutes with a cocoa shell/water ratio of 1 to 5 by weight. This was followed by an extraction step in a hydraulic press to separate the aqueous portion from the cocoa shell fiber portion. The recovered cocoa shell fiber portion was again heated at 60° C. for 10 minutes with a cocoa shell/water ratio of 1 to 5 by weight. After an additional extraction (by pressing), the fibrous portion was then refined in a Valley beater at 1.4% consistency for 10 minutes. After refining, cellulosic fibers (a blend of *abaci*, hardwood and softwood pulps, with the respective ratios: 60/10/30) were added to the cocoa shell fibrous residue with a cocoa shell/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 34% extract content, which is the soluble content of the starting material of the experiment. The coated hand sheets were dried on a plate dryer.

The invention claimed is:

1. A fibrous material comprising:
    a reconstituted cocoa shell material comprising (1) extracted cocoa shell fibers combined with (2) cellulosic fibers, and wherein the reconstituted cocoa shell material does not contain tobacco, and wherein the reconstituted cocoa shell material has been formed into a sheet.

2. A fibrous material as defined in claim 1, wherein the reconstituted cocoa shell material contains water solubles in an amount of less than about 30% by weight.

3. A fibrous material as defined in claim 1, wherein the reconstituted cocoa shell material contains water solubles in an amount of about 5% by weight to about 20% by weight.

4. A fibrous material as defined in claim 1, wherein the cellulosic fibers comprise wood pulp fibers.

5. A fibrous material as defined in claim 1, wherein the cellulosic fibers comprise flax fibers, hemp fibers, abaca fibers, softwood fibers, hardwood fibers, bamboo fibers, coconut fibers, ramie fibers, jute fibers or mixtures thereof.

6. A fibrous material as defined in claim 1, wherein the cellulosic fibers are present in the reconstituted cocoa shell material in a weight ratio to the cocoa shell fibers of from about 20/80 to about 80/20.

7. A fibrous material as defined in claim 1, wherein the cellulosic fibers are present in the reconstituted cocoa shell material in a weight ratio to the cocoa shell fibers of from about 20/80 to about 40/60.

8. A fibrous material as defined in claim 1, wherein the reconstituted cocoa shell material has a basis weight of from about 20 gsm to about 200 gsm.

9. A fibrous material as defined in claim 8, wherein the reconstituted cocoa shell material does not contain tobacco.

10. A fibrous material as defined in claim 1, wherein the reconstituted cocoa shell material has a basis weight of from about 90 gsm to about 120 gsm.

11. A fibrous material as defined in claim 1, further comprising a wet strength agent.

12. A fibrous material as defined in claim 1, wherein an extract obtained from the extracted cocoa fibers has been applied to the reconstituted cocoa shell material.

13. A fibrous material as defined in claim 12, wherein the extract is at least partially penetrated into the reconstituted cocoa shell material.

14. A fibrous material as defined in claim 1, wherein the extracted cocoa shell fibers have been refined prior to forming the reconstituted cocoa shell material.

15. A fibrous material comprising:
    a reconstituted cocoa shell material comprising (1) extracted cocoa shell fibers combined with (2) cellulosic fibers, wherein the reconstituted cocoa shell material contains extracted cocoa shell fibers in an amount of at least about 40% by weight, and wherein the reconstituted cocoa shell material has been formed into a sheet.

16. A fibrous material as defined in claim 15, wherein the extracted cocoa shell fibers have been refined prior to forming the reconstituted cocoa shell material.

17. A fibrous material as defined in claim 15, wherein the cellulosic fibers comprise hemp fibers.

18. A fibrous material comprising:
a reconstituted cocoa shell material comprising (1) extracted cocoa shell fibers combined with (2) cellulosic fibers, the cocoa shell fibers having been extracted by removing water soluble components to produce an insoluble residue fraction, the insoluble residue fraction having been subjected to one or more mechanical refiners to produce a fibrous pulp that is incorporated into the reconstituted cocoa shell material, and wherein the reconstituted cocoa shell material has been formed into a sheet.

19. A fibrous material as defined in claim 18, wherein the reconstituted cocoa shell material contains tobacco.

20. A fibrous material as defined in claim 18, wherein the fibrous material contains hemp fibers.

* * * * *